US008188144B2

(12) United States Patent
McPhail et al.

(10) Patent No.: US 8,188,144 B2
(45) Date of Patent: May 29, 2012

(54) IN VITRO PRESERVATION OF LIVING ANIMAL CELLS AND COMPOUNDS SUITABLE FOR USE IN THE PRESERVATION OF LIVING ANIMAL CELLS

(75) Inventors: Donald Barton McPhail, Aberdeen (GB); Graeme James Cook, Peterhead (GB); Andrew Scott Johnstone, Edinburgh Lothian (GB)

(73) Assignee: Antoxis Limited, Roslin Lothian (GB)

( * ) Notice: Subject to any disclaimer, the term of this patent is extended or adjusted under 35 U.S.C. 154(b) by 0 days.

(21) Appl. No.: 12/757,717

(22) Filed: Apr. 9, 2010

(65) Prior Publication Data

US 2010/0267132 A1     Oct. 21, 2010

Related U.S. Application Data

(63) Continuation-in-part of application No. PCT/GB2008/050931, filed on Oct. 10, 2008.

(30) Foreign Application Priority Data

Oct. 10, 2007   (GB) .................................. 0719751.0

(51) Int. Cl.
*A61K 31/35* (2006.01)
*A61K 31/38* (2006.01)
*A61K 31/40* (2006.01)
*C07D 315/00* (2006.01)
*C07D 207/38* (2006.01)

(52) U.S. Cl. ........ 514/460; 549/418; 548/563; 514/445; 514/408; 514/427; 514/428; 514/429

(58) Field of Classification Search .................. 549/418
See application file for complete search history.

(56) References Cited

U.S. PATENT DOCUMENTS

| 5,912,174 A | 6/1999 | Scheer et al. |
| 2005/0106554 A1 | 5/2005 | Palecek et al. |

FOREIGN PATENT DOCUMENTS

| EP | 1057405 A | 12/2000 |
| EP | 1627565 A1 | 2/2006 |
| JP | 2002255810 A | 9/2002 |
| WO | 2004007475 A | 1/2004 |
| WO | 2005118785 A1 | 12/2005 |
| WO | 2006019366 A | 2/2006 |
| WO | 2008062184 A | 5/2008 |

OTHER PUBLICATIONS

Klopman et al , DN 109:162929, (1988). RN 117016-28-1.*
Abou El Hassan, M., et al. "The New Cardioprotector Monohydroxyethylrutoside Protects Against Doxorubicin-Induced Inflammatory Effects In Vitro" British Journal of Cancer 89:237-362 (2003).
Abou El Hassan, M., et al. "A Comparative Study Between Catalase Gene Therapy and the Cardioprotector Monohydroxyethylrutoside (Monoher) in Protecting Against Doxorubicin-Induced Cardiotoxicity in Vitro" British Journal of Cancer 89:2140-2146 (2003).
Bennett, C. J. et al., "Potential Therapeutic Antioxidants That Combine the Radical Scavenging Ability of Myricetin and the Lipophilic Chain of Vitamin E to Effectively Inhibit Microsomal Lipid Peroxidation" Bioorganic & Medicinal Chemistry, 12(9):2079-2098 (2004).
Dangles, O. et al., "Inhibition of Lipid Peroxidation by Quercetin and Quercetin Derivatives: Antioxidant and Prooxidant Effects" J. Chem. Soc., 6:1215-1222 (2000).
Fukai, T. et al., "1H NMR Checmical Shift of the Flavonol 5-Hydroxy Proton As a Characterization of 6- or 8-Isoprenoid Substitution" Heterocycles, 34(6):1213-1225 (1992).
Kajiya, K. et al., "Relationship Between Antibacterial Activity of (+)-Catechin Derivatives and Their Interaction With a Model Membrane" J. Agric. Food Chem., 52(6):1514-1519 (2004).
Kessler, M. et al., "Anti- and Pro-Oxidant Activity of Rutin and Quercetin Derivatives" Journal of Pharmacy and Pharmacology, 55:131-142 (2003).
Kim, S.R. et al., "Flavonoids of Inula Britannica Protect Cultured Cortical Cells From Necrotic Cell Death Induced by Glutamate" Free Radical Biology & Medicine, 32(7):596-604 (2002).
Phan, T. et al., Phenolic Compounds of Chromolaena Odorata Protect Cultured Skin Cells From Oxidative Damage: Implication for Cutaneous Wound Healing, Biol. Pharm. Bull. 24(12):1373-1379 (2001).
Miranda, C. L. et al., "Antioxidant and Prooxidant Actions of Prenylated and Nonprenylated Chalcones and Flavanones In Vitro" Journal of Agriculture and Food Chemistry, 48(9):3876-3884 (Sep. 2000).
Rice-Evans, C.A., et al., "Structure-Antioxidant Activity Realationships of Flavonoids and Phenolic Acids" Free Radical Biology & Medicine, 20(7):933-956 (1996).
Sutthivaiyakit, S. et al., "Diterpenylated and Prenylated Flavonoids From Macaranga Denticulata" Tetrahedron, 58(18):3619-3622 (2002).

* cited by examiner

*Primary Examiner* — Andrew D Kosar
*Assistant Examiner* — Raymond Covington
(74) *Attorney, Agent, or Firm* — Nixon Peabody LLP

(57) ABSTRACT

The invention is directed to compounds of Formula (I)

Formula (I)

[Chemical structure showing a benzene ring B with substituents $R_{10}$, $R_{11}$, $R_{12}$, $R_{13}$, $R_{14}$ connected to a ring system with carbons $C^1$, $C^2$, $C^4$, $C^5$, $(C^3)_n$ and substituents $R_{20}$, $R_{21}$, $R_{22}$, $R_{23}$, $R_{24}$, $R_{25}$, $R_{26}$, $R_{27}$, $R_{28}$, and X]

or salts thereof. The invention is also directed to use of the compounds of formula (I) in the in vitro preservation of living animal cells. The living cells can be isolated cells, such as stem cells, or groups of cells such as tissue or an organ.

31 Claims, No Drawings

IN VITRO PRESERVATION OF LIVING ANIMAL CELLS AND COMPOUNDS SUITABLE FOR USE IN THE PRESERVATION OF LIVING ANIMAL CELLS

RELATED APPLICATIONS

This application claims benefit under 35 U.S.C. §120 and is a Continuation-in-Part of the International PCT Application Serial No. PCT/GB2008/050931, filed Oct. 10, 2008, which claims the benefit and priority of Great Britain Patent Application Serial No. 0719751.0, filed Oct. 10, 2007. The contents of both applications are incorporated herein by reference in their entirety.

FIELD OF THE INVENTION

This invention is concerned with in vitro preservation of living animal cells and compounds suitable for use in the preservation of living animal cells. In particular, though not exclusively, the present invention concerns in vitro preservation of stem cells and compounds suitable for use in preserving stem cells.

BACKGROUND

Once harvested, in order to remain viable and retain their undifferentiated state, stem cells must be preserved prior to use for medical or research purposes.

It is well known that stem cells can be stored indefinitely if stored at the temperature of liquid nitrogen (−196° C.). However, it is well documented that the process of freezing may cause irreparable damage to the cells and as such, various cryopreservative agents can be added to the cell suspension prior to the freezing process. US2005/0106554 discloses methods and compositions for the cryopreservation of pluripotent cells, in particular human embryonic stem cells. The methods disclosed in US2005/0106554 are shown to exhibit an increase in cell viability and a decrease in cell differentiation when compared with conventional methods. The cryopreservation method disclosed in US2005/0106554 comprises encapsulation of the cells between two layers of a solid support matrix, adding a cryopreservative to the matrix-cell-matrix composition, and cooling said composition to a temperature sufficient to cryopreserve the cells. US2005/0106554 discloses a carbohydrate-based medium, preferably trehalose, as a suitable cryopreservative. WO2005/118785 discloses methods for the cryopreservation of stem cells, wherein said method includes performing ice nucleation on a cell suspension prior to the reduction of temperature sufficient to allow long term storage of the stem cells. WO2005/118785 further discloses that the cell suspension may or may not contain any exogenous biological cryoprotectant, such as serum.

A number of non-cryogenic methods of stem cell preservation are also known. In such methods, stem cells are generally stored as a cell dispersion in an aqueous solution containing tissue cell culture growth media. Often a preservative compound is included in such aqueous solutions so as to reduce the rate at which cell viability decreases. In a typical example, U.S. Pat. No. 5,912,174 discloses a method of storing a population of mammalian cells capable of duplication and differentiation by suspending said population of cells in an aqueous mixture containing gelatin. Preferred mixtures contain standard tissue cell culture growth media such as RMPI or Eagle's media. Optionally, cell-specific growth factor may also be added to preserve cell viability and, for optimum storage life, the storage temperature should be maintained between 0 and 4° C. Further, EP-A-1057405 discloses the use of an aqueous storage liquid comprising polyphenol and a storage liquid selected from Euro-Collin's solution, UW solution, serum and antibiotic solution for the in vitro freeze-free preservation of, inter alia, a stem cell, tissue or organ for transplantation. The polyphenols disclosed in EP-A-1057405 include catechins such as epigallocatechin, tannic acid, proanto-dianisidine, resorcinol, hydroquinone, pyrogallol, phloroglucinol, eugenol and quercetin. There is no suggestion in EP-A-1057405 to the effect that any of the disclosed compounds may preserve the viability of undifferentiated cells. EP1627565 discloses a medium for storing biological samples in a refrigerated, frozen or vitrified state, comprising a balanced salt solution and 4-thioderivative of flavon-3-ol. WO 2006/019366 discloses a culture system developed for the culturing of human embryonic stem cells. The culture condition includes culture of the cells in an atmosphere having minimal oxygen, and may include the use of an antioxidant.

The structures of various natural and synthetic flavonoid compounds are known. For example, Heterocycles, Vol. 34, no. 6, pages 1213-1225 (Fukai, et al.) discloses the use of $^1$H-NMR in order to identify isoprenoid substituted flavanols. The structures of various flavonoids are also proposed. Tetrahedron, Vol. 58, no. 18, pages 2619-2622 (Sutthivaiyakit, et al.) discloses the purification of various flavonoids from the chloroform extract of dried leaves of *M. denticulata*.

The potential therapeutic use of certain flavonoid compounds as antioxidants for the treatment of patients having a disease or disorder involving oxidative damage, such as cancer, heart disease, neurological disorders, auto-immune disorders, ischemia-reperfusion injury, diabetic complications, septic shock, hepatitis, atherosclerosis and complications arising from HIV or Hepatitis B is known from. WO 2004/007475. WO 2004/007475 also discloses the potential application of the flavonoid compounds in sunscreen compositions and skincare compositions. In addition, WO 2004/007475 discloses the potential use of the flavonoid compounds as foodstuff stabilizers, where the ability of the compounds to combat free radicals is considered to be of utility in preventing or delaying the deterioration in food quality during storage. However, whilst WO 2004/007475 discloses the use of the flavonoid compounds for the in vivo therapeutic treatment of living matter and for the in vitro stabilizing treatment of dead matter, there is no disclosure or suggestion that the flavonoid compounds would be useful for in vitro preservation of living matter.

J. Agric. Food Chem., Vol. 48, pages 3876-3884 (Miranda et al.), disclosed test of certain flavanoid compounds to inhibit in vitro oxidation of human low density lipoprotein. British Journal of Cancer, 2003, Vol. 89(2), pages 357-362, and Vol. 89(11), pages 2140-2146, disclose the use of monoHER as providing protection against doxorubicin-induced inflammatory effects in vitro and against doxorubicin-induced cardiotoxicity in vitro, based on protection of human umbilical cord vascular endothelial cells and neonatal rat cardiac mycocytes, respectively. Both cell types are fully differentiated.

Free Radical Biology & Medicine, 2002, Vol. 32(7), pages 596-604, disclose the testing of certain flavonoids for protecting primary cultures of rat cortical cells against oxidative stress. The cell types are fully differentiated. Bio. & Pharm. Bull., 2001, Vol. 24(12) pages 1373-1379, disclose in vitro protective effect of mixtures of extracts from certain plants, including some flavonoids, against oxidative stress on human skin cells. The cell types are fully differentiated. Bioorganic & Medicinal Chemistry, Vol. 12, no. 9, pages 2079-2098 (Bennett, et al.) discloses potentially therapeutic antioxidants wherein $C_6$-$C_{12}$ alkyl chains are attached to the A-ring of either a 3,3',4',5'-tetrahydroxyflavone or a 3,2',4',5'-tetrahydroxyflavone head group. J. Agric. Food Chem., Vol. 52, no. 6, pages 1514-1519 (Kajiya, et al.) disclosed tests of the antibacterial activity of certain flavonoid compounds. JP 2002 255810 A discloses catechin derivatives which possess improved antimicrobial properties in comparison to naturally occurring catechins. Journal of Pharmacy and Pharmacology, Vol. 55, no. 1, pages 131-142 (Kessler, et al.) and J. Chem. Soc. Vol. 6, pages 1215-1222 (Dangles, et al.) both disclose the biochemical evaluation of the effect of quercertin and quercertin derivatives such as its 3-O-glycoside rutin on lipid peroxidation. Both Kessler, et al. and Dangles, et al. suggest that flavonoids can act both as antioxidants and pro-oxidants under certain conditions.

WO 2008/062184, published after the priority date of the present application, discloses various flavonoid-type compounds which function as fluorescent probes and antioxidants and may be useful in discriminating healthy and stressed cells.

The object of the present invention is to provide an improved method for the in vitro preservation of living animal cells. In particular, it is an object of the present invention to provide an improved method for the in vitro preservation of a mammalian cell, tissue or organ for research or medical purposes e.g. transplantation. More preferred, it is an object of the present invention to provide an improved method for the in vitro preservation of stem cells.

THE INVENTION

The invention in its various aspects is as set out in the accompanying claims.

In a first aspect, the present invention provides a method for in vitro preservation of living animal cells, said method comprising contacting said living animal cells with a compound of Formula I or a salt thereof:

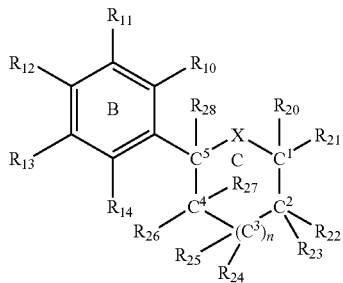

Formula I wherein:
A) $R_{12}$ and $R_{26}$ each independently represent —OH or a glycosidic functional group; $R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$ alkoxy-, hydroxy-$C_{1-6}$alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;

B) either a):
$R_{20}$ represents H or a $C_{2-30}$ saturated or unsaturated hydrocarbon chain;
$R_{21}$:
i) represents H;
ii) together with $R_{22}$ provides a second bond between $C^1$ and $C^2$.
iii) when X is —$NR_1$— and $R_1$ is not H or $C_{1-6}$alkyl, together with $R_1$ provides a second bond between $C^1$ and N;
$R_{22}$:
i) represents H;
ii) together with $R_{23}$ forms =O; or
iii) together with $R_2$, provides a second bond between $C^1$ and $C^2$;
$R_{23}$:
i) represents H or a $C_{2-30}$ saturated or unsaturated hydrocarbon chain; or
ii) together with $R_{22}$ forms =O;
wherein at least one of $R_{20}$ and $R_{23}$ is a $C_{2-30}$ saturated or unsaturated hydrocarbon chain;
or b):
$R_{20}$, $R_{21}$, $R_{22}$, and $R_{23}$ form part of a 5, 6 or 7 membered unsaturated-ring including $C^1$ and $C^2$, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;

C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;

D) X is —O—, —S— or —$NR_1$—, wherein $R_1$ represents i) H or $C_{1-6}$alkyl, or ii) together with $R_2$, provides a second bond between $C^1$ and N;

wherein said $C_{2-30}$ saturated or unsaturated hydrocarbon chain of $R_{20}$, $R_{23}$ and the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —$CO_2$H, —$CO_2C_{1-6}$alkyl, —$S(O)_2C_{1-6}$alkyl, —$S(O)_2$phenyl, —$SC_{1-6}$alkyl, —$NO_2$, —OH, —$CF_3$, —$N(R_2)(R_3)$, —NHC(O)NH$C_{1-6}$alkyl, —C(O)N($R_2$)($R_3$), imine and substituted or unsubstituted triphenylphosphonium; and wherein one or more available —$CH_2$— groups present in the $C_{2-30}$ hydrocarbon chain of $R_{20}$, $R_{23}$ or the 5, 6 or 7 membered unsaturated ring is optionally and independently substituted by —O—, —C(O)—, —$S(O)_p$—, or —$N(R_2)$— provided always that no two such substitutions in the resulting chain are consecutive; wherein $R_2$ and $R_3$ each independently represent H or $C_{1-6}$alkyl, and wherein p is 0 to 2; and wherein the total number of =O on ring C is no greater than 1.

In one embodiment, the present invention provides a method of in vitro preservation of living animal cells in a viable non-terminally differentiated state, said method comprising contacting living non-terminally differentiated animal cells with a compound of Formula I or a salt thereof:

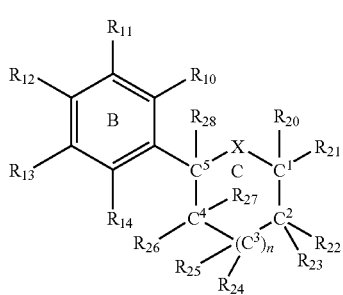

Formula I wherein:
A) $R_{12}$ and $R_{26}$ each independently represent —OH or a glycosidic functional group; $R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;
B) either a):
$R_{20}$ represents H or a $C_{2-30}$ saturated or unsaturated hydrocarbon chain;
$R_{21}$:
i) represents H;
ii) together with $R_{22}$ provides a second bond between $C^1$ and $C^2$; or
iii) when X is —$NR_1$— and $R_1$ is not H or $C_{1-6}$alkyl, together with $R_1$ provides a second bond between $C^1$ and N;
$R_{22}$:
i) represents H;
ii) together with $R_{23}$ forms =O; or
iii) together with $R_2$, provides a second bond between $C^1$ and $C^2$;
$R_{23}$:
i) represents H or a $C_{2-30}$ saturated or unsaturated hydrocarbon chain;
ii) together with $R_{22}$ forms =O;
wherein at least one of $R_{20}$ and $R_{23}$ is a $C_{2-30}$ saturated or unsaturated hydrocarbon chain;
or b):
$R_{20}$, $R_{21}$, $R_{22}$, and $R_{23}$ form part of a 5, 6 or 7 membered unsaturated-ring including $C^1$ and $C^2$, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;
C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;
D) X is —O—, —S— or —$NR_1$—, wherein $R_1$ i) represents H or $C_{1-6}$alkyl, or ii) together with $R_{21}$ provides a second bond between $C^1$ and N;
wherein said $C_{2-30}$ saturated or unsaturated hydrocarbon chain of $R_{20}$, $R_{23}$ and the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —$CO_2H$, —$CO_2C_{1-6}$alkyl, —$S(O)_2C_{1-6}$alkyl, —$S(O)_2$phenyl, —$SC_{1-6}$alkyl, —$NO_2$, —OH, —$CF_3$, —$N(R_2)(R_3)$, —$NHC(O)NHC_{1-6}$alkyl, —$C(O)N(R_2)(R_3)$, imine and substituted or unsubstituted triphenylphosphonium; and wherein one or more available —$CH_2$— groups present in the $C_{2-30}$ hydrocarbon chain of $R_{20}$, $R_{23}$ and the 5, 6 or 7 membered unsaturated ring is optionally and independently replaced by —O—, —C(O)—, —$S(O)_p$—, or —$N(R_2)$— provided always that no two such replacements in the resulting chain are consecutive; wherein $R_2$ and $R_3$ each independently represent H or $C_{1-6}$alkyl, and wherein p is 0 to 2; and
wherein the total number of =O on ring C is no greater than 1.

In another embodiment, the present invention provides a method for in vitro preservation of living animal cells wherein said living animal cells are in the form of a tissue or an organ, said method comprising contacting said living animal cells with a compound of Formula I or a salt thereof:

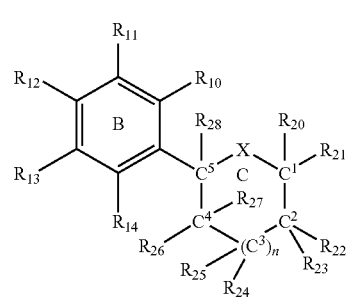

Formula I wherein:
A) $R_{12}$ and $R_{26}$ each independently represent —OH or a glycosidic functional group; $R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;

B) either a):
  $R_{20}$ represents H or a $C_{2-30}$ saturated or unsaturated hydrocarbon chain;
  $R_{21}$:
    i) represents H;
    ii) together with $R_{22}$ provides a second bond between $C^1$ and $C^2$; or
    iii) when X is —$NR_1$— and $R_1$ is not H or $C_{1-6}$alkyl, together with $R_1$ provides a second bond between $C^1$ and N;
  $R_{22}$:
    i) represents H;
    ii) together with $R_{23}$ forms =O; or
    iii) together with $R_2$, provides a second bond between $C^1$ and $C^2$;
  $R_{23}$:
    i) represents H or a $C_{2-30}$ saturated or unsaturated hydrocarbon chain; or
    ii) together with $R_{22}$ forms =O;
  wherein at least one of $R_{20}$ and $R_{23}$ is a $C_{2-30}$ saturated or unsaturated hydrocarbon chain;
  or b):
    $R_{20}$, $R_{21}$, $R_{22}$, and $R_{23}$ form part of a 5, 6 or 7 membered unsaturated-ring including $C^1$ and $C^2$, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;
C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;
D) X is —O—, —S— or wherein $R_1$ represents i) H or $C_{1-6}$alkyl, or ii) together with $R_{21}$ provides a second bond between $C^1$ and N;
wherein said $C_{2-30}$ saturated or unsaturated hydrocarbon chain of $R_{20}$, $R_{23}$ and the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —$CO_2H$, —$CO_2C_{1-6}$alkyl, —$S(O)_2C_{1-6}$alkyl, —$S(O)_2$phenyl, —$SC_{1-6}$alkyl, —$NO_2$, —OH, —$CF_3$, —$N(R_2)(R_3)$, —$NHC(O)NHC_{1-6}$alkyl, —$C(O)N(R_2)(R_3)$, imine and substituted or unsubstituted triphenylphosphonium; and wherein one or more available —$CH_2$— groups present in the $C_{2-30}$ hydrocarbon chain of $R_{20}$, $R_{23}$ or? the 5, 6 or 7 membered unsaturated ring is optionally and independently substituted by —O—, —C(O)—, —$S(O)_p$—, or —$N(R_2)$— provided always that no two such substitutions in the resulting chain are consecutive; wherein $R_2$ and $R_3$ each independently represent H or $C_{1-6}$alkyl, and wherein p is 0 to 2; and wherein the total number of =O on ring C is no greater than 1.

As well as concerning a method for the in vitro preservation of living animal cells, the present invention is also concerned with novel compounds. Surprisingly, these novel compounds have been found to be suitable for use as preservatives for living animal cells.

Accordingly, in another aspect of the present invention, there is provided a compound of Formula Ia or a salt thereof:

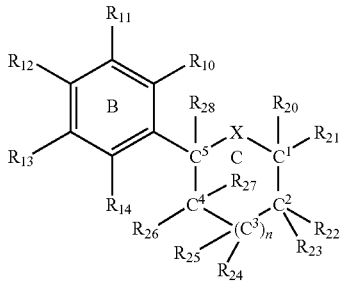

Formula Ia wherein:
A) $R_{12}$ and $R_{26}$ each independently represent —OH or a glycosidic functional group; $R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;
B) either a):
  $R_{20}$ represents H or a $C_{2-30}$ saturated or unsaturated hydrocarbon chain;
  $R_{21}$:
    i) represents H;
    ii) together with $R_{22}$ provides a second bond between $C^1$ and $C^2$, or
    iii) when X is —$NR_1$— and $R_1$ is not H or $C_{1-6}$alkyl, together with $R_1$ provides a second bond between $C^1$ and N;
  $R_{22}$:
    i) represents H;
    ii) together with $R_{23}$ forms =O; or
    iii) together with $R_{21}$ provides a second bond between $C^1$ and $C^2$;
  $R_{23}$:
    i) represents H or a $C_{2-30}$ saturated or unsaturated hydrocarbon chain; or
    ii) together with $R_{22}$ forms =O;
  wherein at least one of $R_{20}$ and $R_{23}$ is a $C_{2-30}$ saturated or unsaturated hydrocarbon chain;
  or b):
    $R_{20}$, $R_{21}$, $R_{22}$, and $R_{23}$ form part of a 5, 6 or 7 membered unsaturated-ring including $C^1$ and $C^2$, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-30}$ cchydrocarbon chain may be substituted with one or more of nitro, halogen, amino, amido, cyano, carboxyl, sulphonyl, ketone, aldehyde or nitrone groups;
C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;

D) X is —O—, —S— or —NR$_1$—, wherein R$_1$ represents i) H or C$_{1-6}$alkyl, or ii) together with R$_2$, provides a second bond between C$^1$ and N;

wherein said C$_{2-30}$ saturated or unsaturated hydrocarbon chain of R$_{20}$, R$_{23}$ and the 5, 6 or 7 membered unsaturated ring is optionally and independently substituted with one or more groups selected from C$_{1-6}$ alkyl, C$_{1-6}$alkoxy, hydroxy-C$_{1-6}$ alkyl, Cl, F, Br, I, —CN, —CO$_2$H, —CO$_2$C$_{1-6}$alkyl, —S(O)$_2$C$_{1-6}$alkyl, —S(O)$_2$phenyl, —SC$_{1-6}$alkyl, —NO$_2$, —OH, —CF$_3$, —N(R$_2$)(R$_3$), —NHC(O)NHC$_{1-6}$alkyl, —C(O)N(R$_2$)(R$_3$), imine and substituted or unsubstituted triphenylphosphonium; and wherein one or more available —CH$_2$— groups present in the C$_{2-30}$ hydrocarbon chain of R$_{20}$, R$_{23}$ or the 5, 6 or 7 membered unsaturated ring is optionally and independently replaced by —O—, —C(O)—, —S(O)$_p$—, or —N(R$_2$)— provided always that the resulting chain includes a —CH$_2$— group connecting to C$^1$, C$^2$ or the 5, 6 or 7 membered ring and no two such replacements are consecutive; wherein R$_2$ and R$_3$ each independently represent H or C$_{1-6}$alkyl, and wherein p is 0 to 2; and wherein the total number of =O on ring C is no greater than 1;

provided that when i) n=1, ii) X represents —O—, iii) R$_{12}$ represents —OH, iv) R$_{24}$ together with R$_{25}$ represent =O, v) R$_{20}$, R$_{21}$, R$_{22}$ and R$_{23}$ form a benzene ring including C$^1$ and C$^2$, and vi) said benzene ring is substituted with at least one group which is a C$_{2-30}$ saturated or unsaturated hydrocarbon chain, then:

said C$_{2-30}$ saturated or unsaturated hydrocarbon chain is substituted with one or more groups selected from C$_{1-6}$alkoxy, hydroxy-C$_{1-6}$ alkyl, Cl, F, Br, I, —CN, —CO$_2$H, sulphonyl, —CO$_2$C$_{1-6}$alkyl, —S(O)$_2$C$_{1-6}$ alkyl, —S(O)$_2$phenyl, —SC$_{1-6}$alkyl, —NO$_2$, —OH, —CF$_3$, —N(R$_2$)(R$_3$), —NHC(O)NHC$_{1-6}$alkyl, —C(O)N(R$_2$)(R$_3$), imine and substituted or unsubstituted triphenylphosphonium; and/or wherein one or more available —CH$_2$-groups present in said C$_{2-30}$ hydrocarbon chain is replaced by —O—, —C(O)—, —S(O)$_p$—, or —N(R$_2$)—; wherein R$_2$ and R$_3$ each independently represent H or C$_{1-6}$alkyl, and wherein p is 0 to 2; and/or said benzene ring is substituted with one or more groups selected from nitro, halogen, amino, amido, cyano, carboxyl, sulphonyl, ketone, aldehyde and saturated or unsaturated C$_{1-6}$ hydrocarbon chain, which C$_{1-6}$ hydrocarbon chain is substituted with one or more of nitro, halogen, amino, amido, cyano, carboxyl, sulphonyl, hydroxyl, ketone, aldehyde or nitrone groups.

In each aspect of the present invention, the compound of Formula I or Ia or salt thereof may be a compound of Formula II or a salt thereof:

Formula II

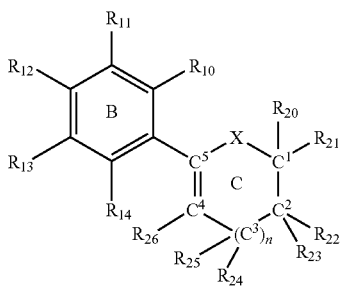

wherein:

A) R$_{12}$ and R$_{26}$ each independently represent —OH or a glycosidic functional group; R$_{10}$, R$_{11}$, R$_{13}$ and R$_{14}$ each independently represent H, —OH, nitro, halogen, amino, amido, cyano, carboxyl, sulphonyl, a glycosidic functional group, C$_{1-6}$ alkoxy-, hydroxyC$_{1-6}$ alkyl-, C$_{1-6}$ alkoxy-C$_{1-6}$ alkyl-, or a saturated or unsaturated C$_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;

B) either a):

R$_{20}$ represents H or a C$_{2-30}$ saturated or unsaturated hydrocarbon chain;

R$_{21}$:
  i) represents H;
  ii) together with R$_{22}$ provides a second bond between C$^1$ and C$^2$; or
  iii) when X is —NR$_1$— and R$_1$ is not H or C$_{1-6}$ alkyl, together with R$_1$ provides a second bond between C$^1$ and N;

R$_{22}$:
  i) represents H;
  ii) together with R$_{23}$ forms =O; or
  iii) together with R$_{21}$ provides a second bond between C$^1$ and C$^2$; and R$_{23}$:
  i) represents H or a C$_{2-30}$ saturated or unsaturated hydrocarbon chain; or
  ii) together with R$_{22}$ forms =O;

wherein at least one of R$_{20}$ and R$_{23}$ is a C$_{2-30}$ saturated or unsaturated hydrocarbon chain;

or b)

R$_{20}$, R$_{21}$, R$_{22}$ and R$_{23}$ form part of a 5, 6 or 7 membered unsaturated-ring including C$^1$ and C$^2$("A" ring), which ring is substituted with at least one group which is a C$_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated C$_{2-15}$ hydrocarbon chain, which C$_{2-15}$ hydrocarbon chain may be substituted with one or more of nitro, halogen, amino, amido, cyano, carboxyl, sulphonyl, hydroxyl, ketone, aldehyde or nitrone groups;

C) n is 0 or 1, wherein when n is 1, either i) R$_{24}$ and R$_{25}$ together form =O, or ii) R$_{24}$ and R$_{25}$ represent H;

D) X is —O—, —S— or wherein R$_1$ represents i) H or C$_{1-6}$alkyl, or ii) together with R$_2$, provides a second bond between C$^1$ and N;

wherein said C$_{2-30}$ saturated or unsaturated hydrocarbon chain of R$_{20}$, R$_{23}$ or the 5, 6 or 7 membered unsaturated ring is optionally and independently substituted with one or more groups selected from C$_{1-6}$ alkyl, C$_{1-6}$alkoxy, hydroxy-C$_{1-6}$ alkyl, Cl, F, Br, I, —CN, —CO$_2$H, —CO$_2$C$_{1-6}$alkyl, —S(O)$_2$C$_{1-6}$alkyl, —S(O)$_2$phenyl, —SC$_{1-6}$alkyl, —NO$_2$, —OH, —CF$_3$, —N(R$_2$)(R$_3$), —NHC(O)NHC$_{1-6}$alkyl, —C(O)N(R$_2$)(R$_3$), imine and substituted or unsubstituted triphenylphosphonium; wherein one or more available —CH$_2$— groups present in the C$_{2-30}$ hydrocarbon chain of R$_{20}$, R$_{23}$ or the 5, 6 or 7 membered unsaturated ring is optionally and independently replaced by —O—, —C(O)—, —S(O)$_p$—, or —N(R$_2$)— provided always that no two such substitutions in the resulting chain are consecutive; wherein R$_2$ and R$_3$ each independently represent H or C$_{1-6}$alkyl, and wherein p is 0 to 2; and wherein the total number of =O on ring C is no greater than 1.

In each aspect of the present invention, X may be O.

In some embodiments of each aspect of the present invention n=0. In other embodiments of each aspect of the present invention n=1.

In some embodiments of each aspect of the present invention, R$_{20}$ represents H or a C$_{2-30}$ saturated or unsaturated hydrocarbon chain;

R$_{21}$:
  i) represents H; or
  ii) together with R$_{22}$ provides a second bond between C$^1$ and C$^2$;

$R_{22}$:
i) represents H;
ii) together with $R_{23}$ forms =O; or
iii) together with $R_2$, provides a second bond between $C^1$ and $C^2$; and $R_{23}$:
i) represents H or a $C_{2-30}$ saturated or unsaturated hydrocarbon chain; or
ii) together with $R_{22}$ forms =O;
wherein at least one of $R_{20}$ and $R_{23}$ is a $C_{2-30}$ saturated or unsaturated hydrocarbon chain;

In each aspect of the present invention, $R_{12}$ and $R_{26}$ may both represent OH or they may both represent a glycosidic functional group; and/or one but not both of $R_{12}$ and $R_{26}$ may represent a glycosidic functional group, for example $R_{12}$ may be OH when $R_{26}$ is a glycosidic functional group or visa versa; and/or one or both of $R_{11}$ and $R_{13}$ may represent OH; and/or $R_{10}$ and $R_{14}$ each independently represent H, OH or $C_{1-6}$alkoxy-. An example of such a compound, wherein X=O and $R_{27}$ together with $R_{28}$ provides a second bond between $C^4$ and $C^5$ is the compound of Formula III or a salt thereof:

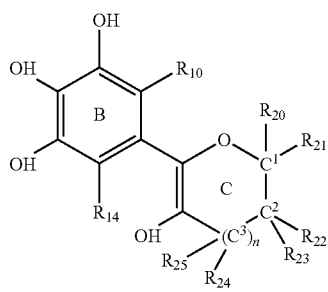

Formula III wherein:
A) $R_{10}$ and $R_{14}$ each independently represent H, —OH, nitro, halogen, amino, amido, cyano, carboxyl, sulphonyl, a glycosidic functional group, $C_{1-6}$ alkoxy-, hydroxy$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;

B) either a):
$R_{20}$ represents H or a $C_{2-30}$ saturated or unsaturated hydrocarbon chain;
$R_{21}$:
i) represents H; or
ii) together with $R_{22}$ provides a second bond between $C^1$ and $C^2$;
$R_{22}$:
i) represents H;
ii) together with $R_{23}$ forms =O; or
iii) together with $R_2$, provides a second bond between $C^1$ and $C^2$; and
$R_{23}$:
i) represents H or a $C_{2-30}$ saturated or unsaturated hydrocarbon chain; or
ii) together with $R_{22}$ forms =O;
wherein at least one of $R_{20}$ and $R_{23}$ is a $C_{2-30}$ saturated or unsaturated hydrocarbon chain;

or b)
$R_{20}$, $R_{21}$, $R_{22}$ and $R_{23}$ form part of a 5, 6 or 7 membered unsaturated-ring including $C^1$ and $C^2$ ("A" ring), which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;

C) n is 0 or 1, wherein when n is 1, either i) $R_{24}$ and $R_{25}$ together form =O, or ii) $R_{24}$ and $R_{25}$ represent H;
wherein said $C_{2-30}$ saturated or unsaturated hydrocarbon chain of $R_{20}$, $R_{23}$ or the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —CO$_2$H, —CO$_2C_{1-6}$alkyl, —S(O)$_2C_{1-6}$alkyl, —S(O)$_2$phenyl, —SC$_{1-6}$alkyl, —NO$_2$, —OH, —CF$_3$, —N(R$_2$)(R$_3$), —NHC(O)NHC$_{1-6}$alkyl, —C(O)N(R$_2$)(R$_3$), imine and substituted or unsubstituted triphenylphosphonium; wherein one or more available —CH$_2$— groups present in the $C_{2-30}$ hydrocarbon chain of $R_{20}$, $R_{23}$ or the 5, 6 or 7 membered unsaturated ring is optionally and independently replaced by —O—, —C(O)—, —S(O)$_p$—, or —N(R$_2$)— provided always that no two such replacements in the resulting chain are consecutive; wherein $R_2$ and $R_3$ each independently represent H or $C_{1-6}$alkyl, and wherein p is 0 to 2; and
wherein the total number of =O on ring C is no greater than 1. A further example of such a compound, but wherein X=O, n=1, $R_{24}$ together with $R_{25}$ forms =O and $R_{27}$ together with $R_{28}$ provides a second bond between $C^4$ and $C^5$, is the compound of Formula VI or salt thereof:

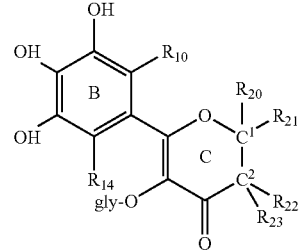

Formula VI wherein:
A) $R_{10}$ and $R_{14}$ each independently represent H, —OH, nitro, halogen, amino, amido, cyano, carboxyl, sulphonyl, a glycosidic functional group, $C_{1-6}$ alkoxy-hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group; and —O-gly represents a glycosidic functional group;

B) either a):
$R_{20}$ represents H or a $C_{2-30}$ saturated or unsaturated hydrocarbon chain;
$R_{21}$:
i) represents H; or
ii) together with $R_{22}$ provides a second bond between $C^1$ and $C^2$;
$R_{22}$:
i) represents H;
ii) together with $R_{21}$ provides a second bond between $C^1$ and $C^2$; and
$R_{23}$ represents H, or a $C_{2-30}$ saturated or unsaturated hydrocarbon chain;

wherein at least one of $R_{20}$ and $R_{23}$ is a $C_{2-30}$ saturated or unsaturated hydrocarbon chain;

or b)

$R_{20}$, $R_{21}$, $R_{22}$ and $R_{23}$ form part of a 5, 6 or 7 membered unsaturated-ring including $C^1$ and $C^2$, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;

wherein said $C_{2-30}$ saturated or unsaturated hydrocarbon chain of $R_{20}$, $R_{23}$ or the 5, 6 or 7 membered unsaturated ring is optionally and independently substituted with one or more groups selected from $C_{1-6}$ alkyl, $C_{1-6}$alkoxy, hydroxy-$C_{1-6}$alkyl, Cl, F, Br, I, —CN, —$CO_2H$, —$CO_2C_{1-6}$alkyl, —$S(O)_2C_{1-6}$alkyl, —$S(O)_2$phenyl, —$SC_{1-6}$alkyl, —$NO_2$, —OH, —$CF_3$, —$N(R_2)(R_3)$, —$NHC(O)NHC_{1-6}$alkyl, —$C(O)N(R_2)(R_3)$, imine and substituted or unsubstituted triphenylphosphonium; wherein one or more available —$CH_2$— groups present in the $C_{2-30}$ hydrocarbon chain of $R_{20}$, $R_{23}$ or the 5, 6 or 7 membered unsaturated ring is optionally and independently replaced by —O—, —C(O)—, —$S(O)_p$—, or —$N(R_2)$— provided always that no two such replacements in the resulting chain are consecutive; and wherein $R_2$ and $R_3$ each independently represent H or $C_{1-6}$alkyl, and wherein p is 0 to 2.

An example of a compound useful in the first aspect of the present invention where $R_{20}$, $R_{21}$, $R_{22}$ and $R_{23}$ form part of a 5, 6 or 7 membered ring is the compound of Formula VII or a salt thereof:

Formula VII

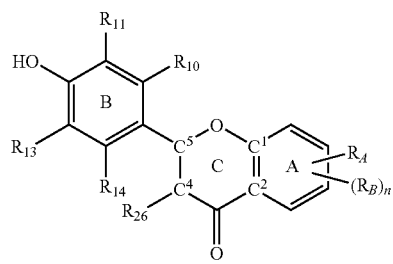

wherein $R_A$ is a $C_2$ to $C_{30}$ saturated or unsaturated hydrocarbon chain;

$R_{10}$, $R_{11}$, $R_{13}$, $R_{14}$ and $R_{26}$ each independently represent H, OH, a $C_{1-6}$ alkoxy, or a saturated or unsaturated $C_{1-6}$ hydrocarbon chain which may be substituted with one or more of nitro, halogen, amino, hydroxyl, ketone or aldehyde group; optionally there is a double bond between $C^4$ and $C^5$ of the C ring; and n represents 0 or 1; and $R_B$ is a $C_2$ to $C_{15}$ saturated or unsaturated hydrocarbon chain, where when $R_B$ is present $R_A$ and $R_B$ are both $C_2$ to $C_{12}$ aliphatic alkyl chains.

The $R_A$ group is preferably substituted on ring A at the para position with respect to $C^2$. The $R_A$ group is preferably a $C_{6-15}$ saturated or unsaturated hydrocarbon chain.

Compounds of Formula VII are disclosed in WO 2004/007475 and as such are specifically excluded from the scope of the second aspect of the present invention.

In both aspects of the present invention, the compound of Formula I or Ia or salt thereof may be an anthocyanin. Anthocyanins are generally known to exist in equilibrium between their hydrated hemiketal form and their flavylium cation form, both of which forms are considered to fall within the scope of the present invention. Anthocyanins within the scope of the present invention are compounds of Formula I or salts thereof wherein:

$R_{12}$ represents OH $R_{26}$ represents a glycosidic functional group $R_{25}$ together with $R_{27}$ provide a second bond between $C^3$ and $C^4$ $R_{28}$ represents OH

X=O, n=1 and $R_{20}$, $R_{21}$, $R_{22}$, and $R_{23}$ form part of a 6 membered unsaturated-ring including $C^1$ and $C^2$, which ring is substituted with at least one group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{1-6}$ hydrocarbon chain, which $C_{1-6}$ hydrocarbon chain may be substituted with one or more of nitro, halogen, amino, amido, cyano, carboxyl, sulphonyl, hydroxyl, ketone, aldehyde or nitrone groups. Anthocyanins within the scope of the present invention can be represented by Formula VIIIHH, which is the structural formula of the compound in its hydrated hemiketal form, and Formula VIIIFC, which is the structural formula of the compound in its flavylium cation form. The flavylium cation form is also in equilibrium with the nonionic flavylium form represented by Formula VIIIFH:

Formula VIIIHH

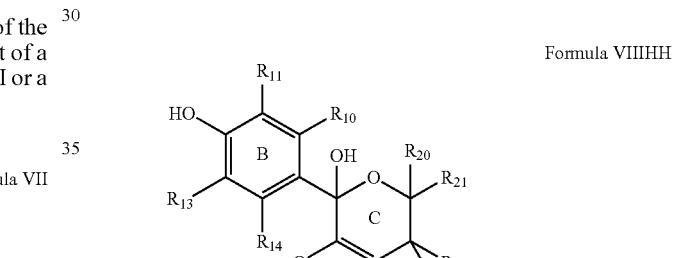

± $H_2O$

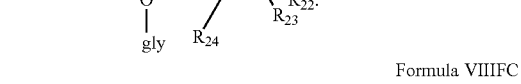

Formula VIIIFC

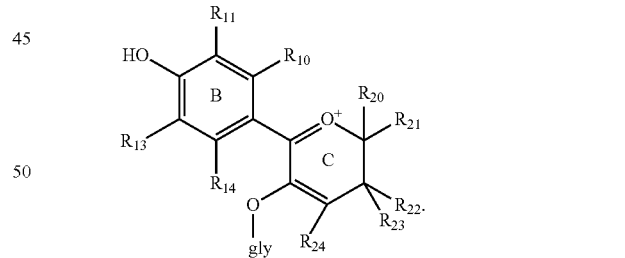

Formula VIIIFH

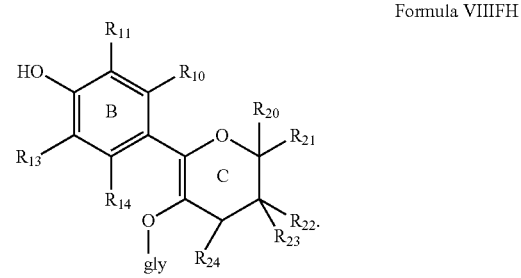

In each aspect of the present invention, when $R_{20}$, $R_{21}$, $R_{22}$, and $R_{23}$ in the compounds of Formula I or Ia or salts thereof form part of a 5, 6 or 7 membered unsaturated-ring including $C^1$ and $C^2$, the ring is substituted with a $C_{2-30}$ saturated or unsaturated hydrocarbon chain, as defined above, at either of the otho, meta or para positions. The ring may be independently further substituted with one or more groups selected from nitro, halogen, amino, amido, cyano, carboxyl, sulphonyl, hydroxyl, ketone, aldehyde and saturated or unsaturated $C_{1-6}$ hydrocarbon chain, which $C_{1-6}$ hydrocarbon chain may be substituted with one or more of nitro, halogen, amino, amido, cyano, carboxyl, sulphonyl, hydroxyl, ketone, aldehyde or nitrone groups. By substitution at the ortho position we mean substitution on a carbon next to the $C^1$ on the ring. By substitution at the meta position we mean substitution on the carbon next to the ortho position remote from $C_1$. By substitution at the para position we mean substitution on the carbon next to the meta position remote from $C^1$. It will be appreciated by those skilled in the art that in the case of 5 membered rings, the para position may also be defined as the meta position. In one embodiment, the compound of Formula I or salt thereof comprises a 5, 6 or 7 membered ring having the $C_{2-30}$ hydrocarbon chain substituted at the meta or para position. For example, the compound of Formula I or salt thereof may comprise a 6 membered ring having the $C_{2-30}$ hydrocarbon substituted at the meta or para position.

The term "glycosidic functional group" is well known in the art, and is represented in the structural formulae herein as —O-gly. For avoidance of any doubt, however, we mean a carbohydrate group linked to the main structure via a glycosidic bond. Preferably, the carbohydrate is a sugar. Preferably the sugar is glucose, rhamnose or rutinose.

In each embodiment of the present invention, the $C_{2-30}$ saturated or unsaturated hydrocarbon chain of $R_{20}$, $R_{23}$ and the 5, 6 or 7 membered unsaturated ring may have from two to twenty carbon atoms, preferably from six to fifteen carbon atoms. Suitably the hydrocarbon chain has a backbone having two, three, four, five, six, seven, eight, nine, ten, eleven, twelve, thirteen, fourteen, fifteen, sixteen, seventeen or eighteen consecutive carbon atoms.

The $C_{2-30}$ saturated or unsaturated hydrocarbon chain of $R_{20}$, $R_{23}$ and the 5, 6 or 7 membered unsaturated ring may include a —$CH_2$— group connecting to $C^1$, $C^2$ or the 5, 6 or 7 membered ring. This means, for example, that the $C_{2-30}$ hydrocarbon chain may not be an alkoxy group, though one or more carbon atoms within the $C_{2-30}$ hydrocarbon chain may be substituted with an alkoxy group. To clarify further, the connection is between a carbon atom on the $C_{2-30}$ saturated or unsaturated hydrocarbon chain and $C^1$, $C^2$ or the 5, 6 or 7 membered ring.

The $C_{2-30}$ saturated or unsaturated hydrocarbon chain of $R_{20}$, $R_{23}$ and the 5, 6 or 7 membered unsaturated ring may be unsubstituted and is preferably saturated. The $C_{2-30}$ saturated or unsaturated hydrocarbon chain of $R_{20}$, $R_{23}$ and the 5, 6 or 7 membered unsaturated ring is preferably a straight hydrocarbon chain preferably comprising 6 to 15 carbon atoms.

When the $C_{2-30}$ saturated or unsaturated hydrocarbon chain is on a 5, 6 or 7 membered unsaturated ring, the ring is optionally and independently further substituted with one or more groups selected from nitro, halogen, amino, amido, cyano, carboxyl, sulphonyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups. In one embodiment, the ring is unsubstituted except for the $C_{2-30}$ hydrocarbon chain. In another embodiment, the ring may be substituted with one or more groups selected from —$NH_2$ and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups.

Examples of specific compounds or salts thereof which are capable of preserving living animal cells include:

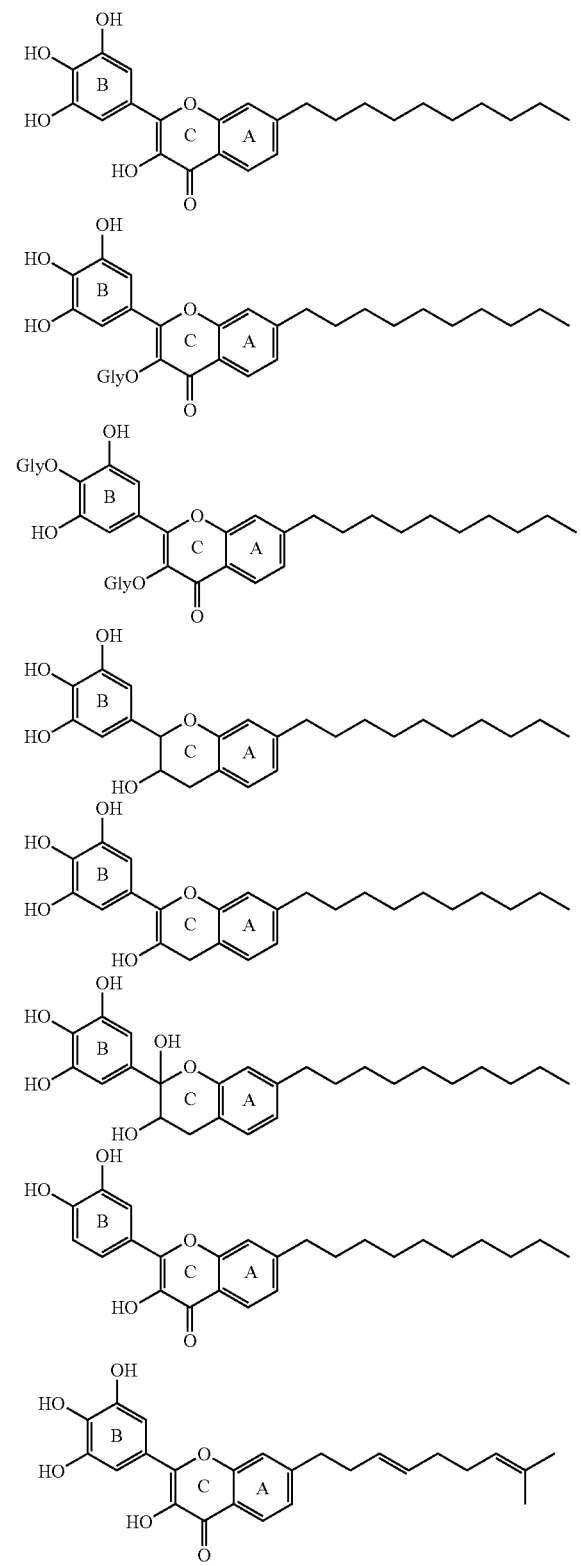

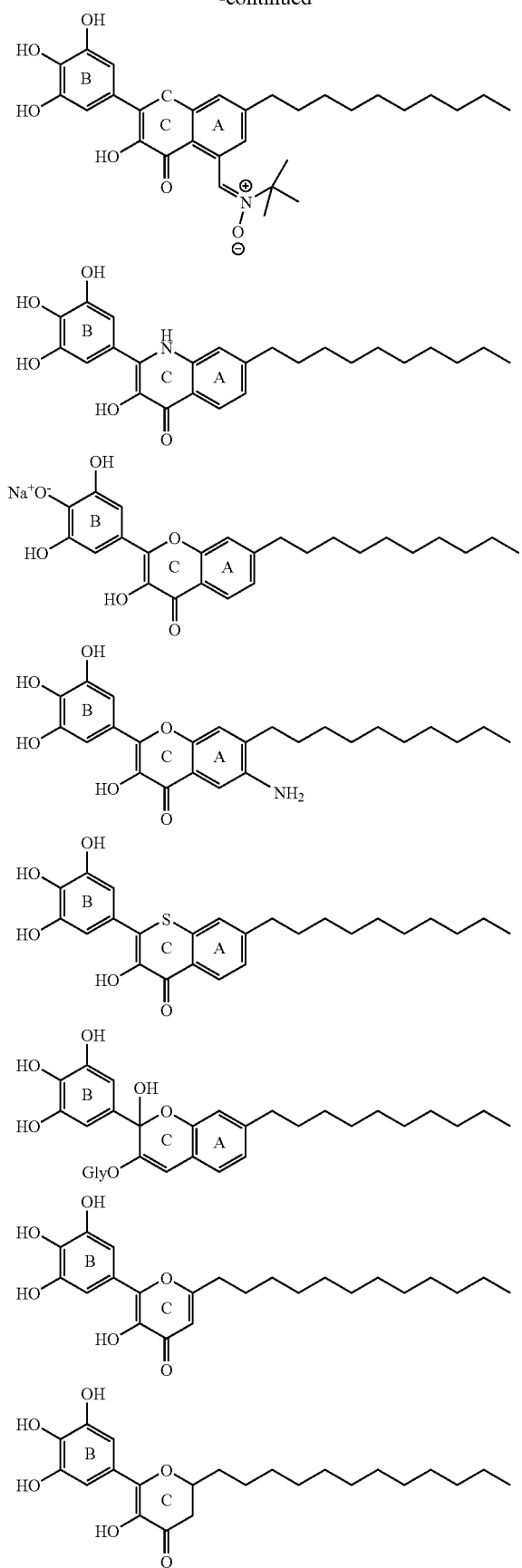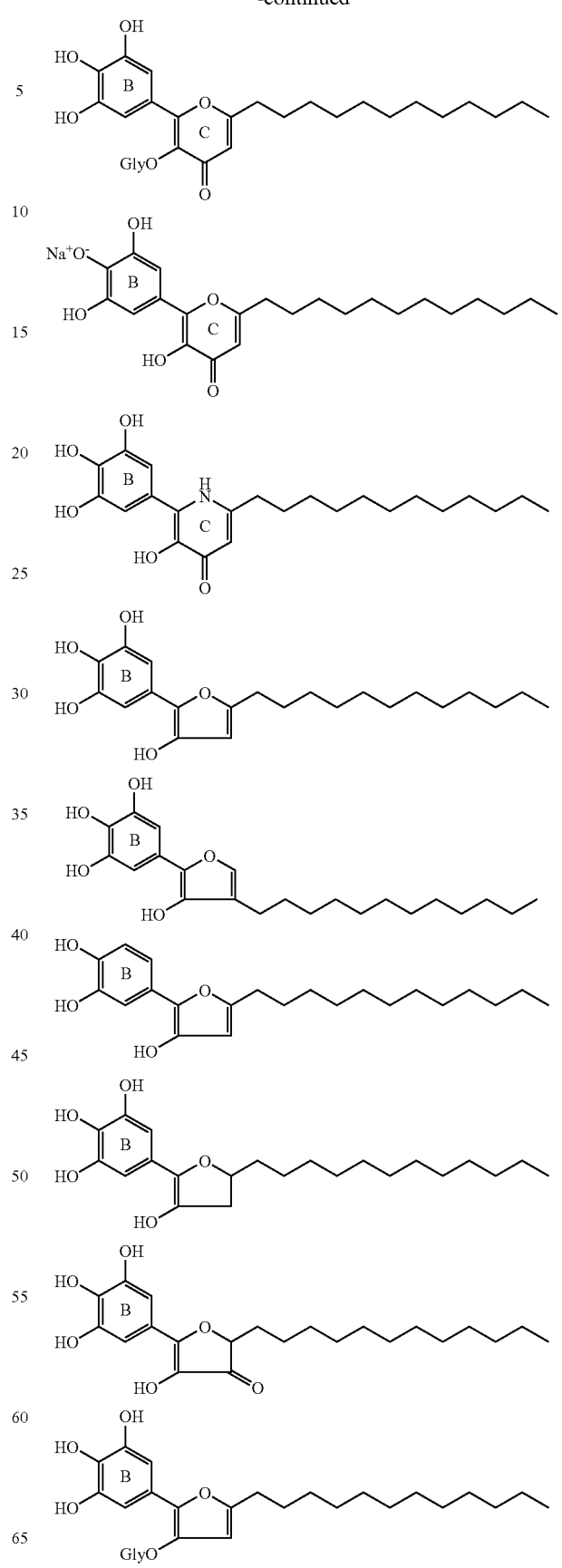

-continued

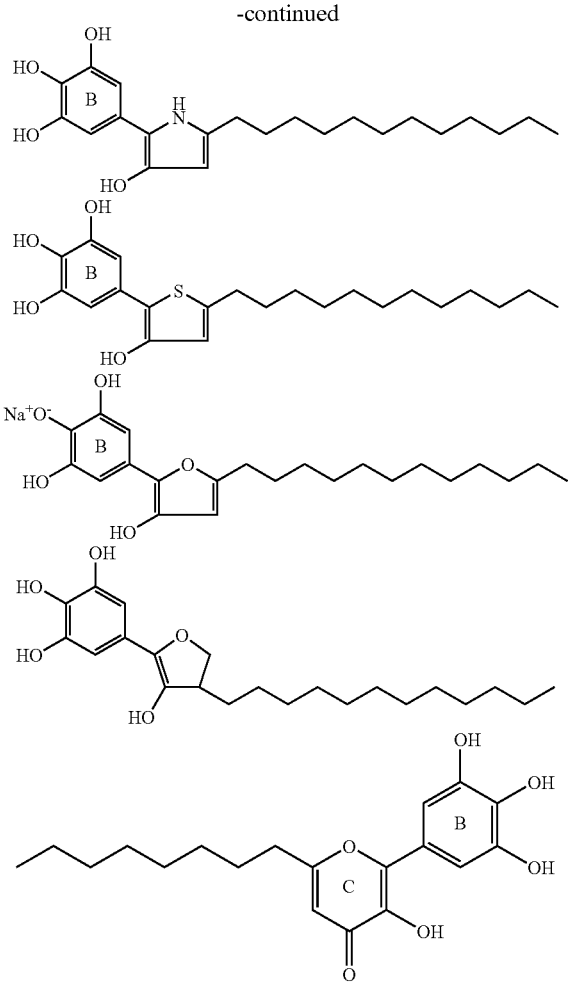

The compounds of the present invention are useful for in vitro preservation of living animal cells. It will be appreciated by those skilled in the art that in some circumstances preservation may not be a permanent state, but here preservation is intended to include a reduction in the rate of deterioration of the viability of individual cells or groups of cells. The expression "in vitro preservation of living animal cells" will be well understood by those skilled in the art but, should any doubt arise, it is intended to mean the in vitro preservation of individual cells or groups of cells, including tissues and organs. As well as being useful for in vitro research purposes, it will be appreciated by persons skilled in the art that such in vitro preservation of the cells or groups of cells may be for eventual autologous, isogenic, allogenic or xenogenic transplantation.

For example, the compounds of the invention may be used in the in vitro preservation of viable terminally differentiated cells e.g. red blood cells and lymphocyte cells such as t-cells and b-cells. Said one or more terminally differentiated cells can be in the form of individual unipotent stem cells or in the form of tissue i.e. a collection of interconnected cells that can perform a similar function in vivo. Tissues suitable for preservation include, but are not limited to, epithelium, connective tissue, muscle tissue and nervous tissue. Furthermore, said one or more fully differentiated cells can form or be part of an organ i.e. a group of tissues that can perform a specific function or group of functions in vivo. Organs suitable for preservation include, but are not limited to, heart, lungs, brain, eyes, stomach, spleen, bone, pancreas, kidney, liver, intestines, skin and bladder.

The method of the invention is used to preserve living animal cells in a viable non-terminally differentiated state. The expression "preservation of living animal cells in a viable non-terminally differentiated state" will be well understood by those skilled in the art but, should any doubt arise, it is intended to include the preservation of living non-terminally differentiated animal cells such that the cells retain the ability to divide and produce at least one non-terminally differentiated cell type.

Differentiation is the process by which an undifferentiated cell becomes differentiated, which in practice means that the undifferentiated cell becomes committed to a particular cell lineage and/or loses its original capacity for differentiating into particular cell types.

Cells that are non-terminally differentiated give rise to various different cell types and can alternatively be described as partially differentiated cells. Such cells include the cells of the three embryonic germ cell layers: endoderm, mesoderm and ectoderm. Cells that are preserved using the methods of the invention also include undifferentiated cells, which have the capacity to differentiate into a multitude of cell types. Undifferentiated cells that are preserved using the methods of the invention are typically stem cells. Cells that are preserved using the methods of the invention also include de-differentiated cells, which are produced when a partially or terminally differentiated cell reverts to an earlier developmental stage. De-differentiated cells can therefore be undifferentiated or partially differentiated. In this aspect, the methods of the invention are particularly useful for the preservation of de-differentiated neuronal cells. In addition, the methods of the invention are useful for the preservation of cells in cell culture which have de-differentiated.

Cells that are non-terminally differentiated include cells that are arrested at a particular stage of the differentiation process or the de-differentiation process. Cells that are non-terminally differentiated therefore include cells that are arrested at a particular stage whilst becoming committed to a particular cell lineage, cells that are arrested at a particular stage whilst reverting to an earlier developmental stage after being non-terminally or terminally differentiated and cells that are re-differentiated after becoming de-differentiated.

In one embodiment, the present invention finds use in the preservation of cells that are differentiated to a non-terminal state of differentiation, i.e. partially differentiated cells, before being transported or stored. The cells can then be induced to a terminally differentiated state when required.

In this aspect of the invention, the cells that are preserved by the methods of the invention can be used for transplantation. Typically, such cells are partially differentiated, and retain the capacity to differentiate into a number of different cell types.

Undifferentiated animal cells which can be preserved using the methods of the invention are typically stem cells. Stem cells are unspecialised cells which are capable of differentiating into various different types of cells and which are capable of self-renewal. Stem cells which can be preserved using a method of the present invention include totipotent stem cells (capable of differentiating into embryonic and extraembryonic cell types), pluripotent stem cells (capable of differentiating into endoderm, mesoderm and ectoderm germ layers), and multipotent stem cells (capable of differentiating into a plurality of closely related cells).

Types of stem cells which can be preserved using the methods of the present invention include embryonic stem (ES) cells (ESCs), adult stem cells and induced pluripotent stem (iPS) cells. Embryonic stem cells are derived from the blastocyst of a mammalian embryo and are totipotent. Embryonic stem cells were originally described by Evans and Kaufman (Nature, 292(5819): 154-156, 1981). Adult stem cells are pluripotent, and include hematopoietic stem cells and mesenchymal stem cells. Induced pluripotent cells are artificially derived from a non-pluripotent cell such as an adult somatic cell by the insertion of certain genes and are very similar to embryonic stem cells (Takahashi et al, Cell 131(5): 861-872, 2007; and Yu et al, Science 318(5858): 1917-1920, 2007). Stem cells are also found in the blood of the umbilical cord, and such umbilical cord blood stem cells can also be preserved using the methods of the present invention.

Stem cells which can be preserved using the methods of present invention can be human or non-human. Typically, the stem cell is a mouse embryonic stem cell or a human embryonic stem cell. Stem cells which can be preserved using the methods of present invention include transgenic stem cells. Stem cells which can be preserved using the methods of present invention also include those produced from hybrid embryos or cytoplasmic hybrid (cybrid) embryos.

Other types of undifferentiated cells which can be preserved using the methods of the present invention include embryonic germ (EG) cells and embryonic carcinoma (EC) cells.

Undifferentiated cells can be identified, for example, by expression of particular marker genes. For example, stem cells can be identified by the expression of the marker genes Oct3/4 and Nanog. Expression of such marker genes can be determined by any suitable method known in the art, for example VCR.

The undifferentiated animal cells which can be preserved using a method of the present invention are typically mammalian cells. Such mammalian cells include human and non-human cells. For example, non-human cells can be from rodents, such as mice, rats and guinea pigs; ungulates, such as cattle, sheep, goats and pigs; or other mammals such as cats, dogs, horses or rabbits. The animal cells can alternatively be bird cells, for example from chickens or turkeys, or fish cells, for example from zebra fish or salmon.

The compounds of Formula I or salts thereof may be used for preserving living animal cells by any of the relevant methods disclosed in European Patent Publication No. EP-A-1057405, contents of which are herein incorporated by in its entirety.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The following examples will demonstrate some embodiments of the invention. The examples are illustrative, and are not intended to limit, in any manner, the claimed invention.

EXAMPLES

Representative Compound Synthesis

Compounds of Formula I and Ia wherein $R_{20}$, $R_{21}$, $R_{22}$, and $R_{23}$ form part of a 6 membered unsaturated ring including $C^1$ and $C^2$ may be formed by the process described in WO 2004/007475, the contents of which are herein incorporated by reference in its entirety. A person skilled in the art would readily be able to adapt this process for the manufacture of compounds of Formula I or Ia including a 5 or 7 membered ring.

Compounds of Formula I or Ia wherein $R_{20}$, $R_{21}$, $R_{22}$, and $R_{23}$ do not form part of a 6 membered unsaturated ring including $C^1$ and $C^2$ may be formed by the following process.

The use of an in situ quench protocol gave the desired boronic acid which would eventually be used to form the B-ring of the target compound (Scheme 1).

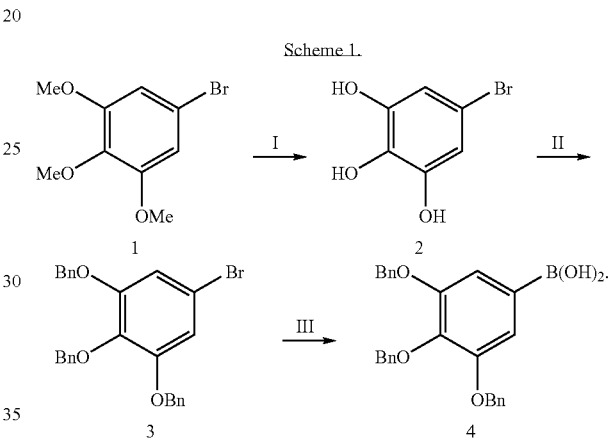

Reagents and conditions: i. BBr3 (1.0M in CH2Cl2, 10 eq.), CH2Cl2, 0° C. to rt, 16 hrs (97%);
ii. BnBr (3.30 eq.), K2CO3 (4.00 eq.), DMF, 100° C., 18 hrs. (57%); iii. t-BuLi (2.20 eq.), B(O-$^i$Pr)3, THF, -78° C. to rt, 16 hrs, (60%).

Phosphonate ester (11) was prepared as follows:

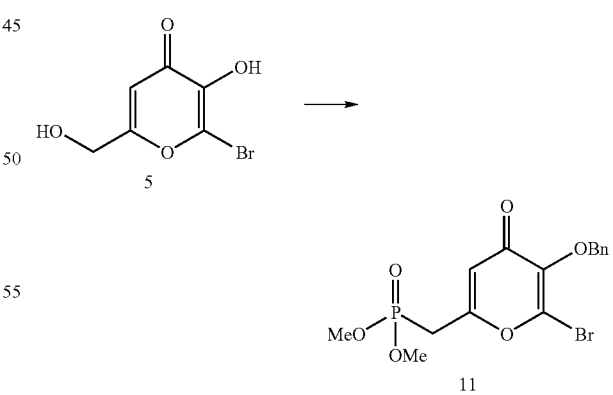

To a stirred solution of 5 (1.88 g, 8.52 mmol, 1.00 eq.) in THF (50 mL) was added benzyl alcohol (4.40 mL, 4.60 g, 42.6 mmol, 5.00 eq.), then triphenylphosphine (2.23 g, 8.52 mmol, 1.00 eq.). The reaction was cooled to 0° C. and DIAD (1.7 mL, 1.72 g, 8.52 mmol, 1.00 eq.) was added dropwise. The reaction was warmed to room temperature and stirred for 4 hours. The reaction mixture was concentrated in vacuo and purified by flash chromatography (10% EtOAc:90% petrol→20% EtOAc:80% petrol→30% EtOAc:70% petrol→50% EtOAc:50% petrol) to yield the benzylated compound as a yellow oil containing about 30% reduced DIAD (1.01 g, 38% including impurity). The crude benzylated compound (535 mg, 1.72 mmol, 1.00 eq.) was diluted with CH$_2$Cl$_2$ (5 mL) and SOCl2 (188 μL, 2.58 mmol, 1.50 eq.) was added at 0° C. The reaction was stirred, with warming to room temperature, for 2.5 hours, when complete by HPLC. The reaction mixture was concentrated in vacuo and purified by flash chromatography (10% EtOAc:90% petrol→20% EtOAc:80% petrol) to yield a brown oil (276 mg, 49%). The chloride (261 mg, 0.79 mmol, 1.00 eq.) was taken into trimethylphosphite (2 mL) and the reaction was heated to reflux and stirred for 16 hours. The reaction was cooled to room temperature and concentrated in vacuo. Purification by flash chromatography (70% EtOAc:30% petrol→100% EtOAc) gave the title phosphonate ester 11 as a brown oil (233 mg, 73%) $^1$H-NMR (400 MHz, CDCl$_3$) 7.47-7.43 (2H, m, 2×ArH), 7.38 7.31 (3H, m, 3×ArH), 6.35 (1H, d, J 3.0, vinylic H), 5.25 (2H, s, OCH$_2$Ar), 3.80 (6H, d, J 11.1, 2×OCH$_3$), 3.07 (2H, d, J 21.7, CH2P).

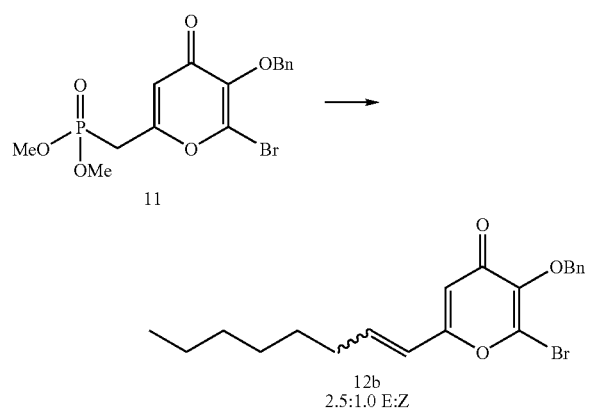

11

To 11 (400 mg, 0.99 mmol, 1.00 eq.) in 1:1 DMF/THF (8 mL) at −78° C. was added LHMDS (1.0 M in THF; 1.10 mL, 1.09 mmol, 1.10 eq.) and the reaction was stirred at that temperature for 10 mins (yellow/orange colour). Heptaldehyde (113 mg, 0.99 mmol, 1.00 eq.) in DMF (4 mL) was added in one portion at −78° C. and the reaction was stirred at that temperature for 45 mins. The reaction was warmed to 0° C. and stirred for 10 mins until complete by HPLC. The reaction was quenched with saturated aqueous ammonium chloride solution (5 mL) and extracted into EtOAc (3×10 mL). The combined organic extracts were washed with water (10 mL) and brine (10 mL), dried (MgSO4) and concentrated in vacuo. Purification by flash chromatography (10% EtOAc: 90% petrol) gave the alkene 12b as a colourless oil and a 2.5:1.0 mixture of E and Z isomers respectively (251 mg, 65%) $^1$H-NMR (400 MHz, CDCl$_3$) 7.50-7.45 (2H, m, 2×ArH), 7.40-7.30 (3H, m, 3×ArH), 6.62 (0.7H, dt, J 15.7 and 7.1, vinylic H), 6.24 (0.3H, s, HC=CO); 6.16 (0.7H, s, HC=CO), 6.08-5.98 (0.3H, m, vinylic H), 6.01 (0.7H, dt, J 15.7 and 1.5, vinylic H), 5.92 (0.3H, dt, J 12.1 and 1.52, vinylic H), 5.28 (0.6H, s, OCH2Ar), 5.26 (1.5H, s, OCH2Ar), 2.46 (0.6H, ddd, J 13.1, 7.5 and 1.5, allylic CH2), 2.24 (1.5H, ddd, J 13.1, 7.5 and 1.5, allylic CH2), 1.52-1.44 (2H, m, CH2), 1.40-1.24 (6H, m, CH2), 0.93-0.88 (3H, m, CH3).

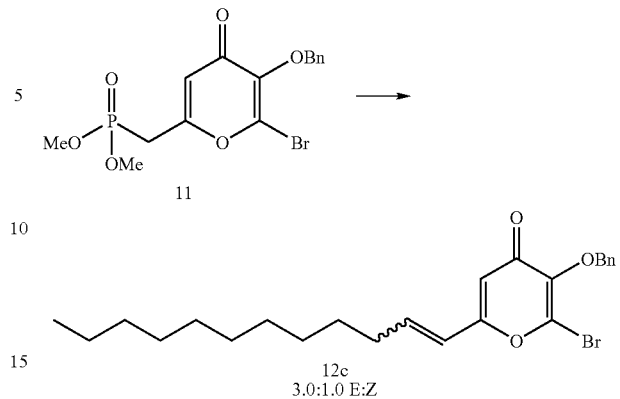

11

To 11 (400 mg, 0.99 mmol, 1.00 eq.) in 1:1 DMF/THF (8 mL) at −78° C. was added LHMDS (1.0 M in THF; 1.10 mL, 1.09 mmol, 1.10 eq.) and the reaction was stirred at that temperature for 10 mins (yellow/orange colour). Undecanal (168 mg, 0.99 mmol, 1.00 eq.) in DMF (4 mL) was added in one portion at −78° C. and the reaction was stirred at that temperature for 45 mins. The reaction was warmed to 0° C. and stirred for 10 mins until complete by HPLC. The reaction was quenched with saturated aqueous ammonium chloride solution (5 mL) and extracted into EtOAc (3×10 mL). The combined organic extracts were washed with water (10 mL) and brine (10 mL), dried (MgSO4) and concentrated in vacuo. Purification by flash chromatography (5% EtOAc:95% petrol→10% EtOAc:petrol) gave the alkene 12c as a colourless oil and an approximate 3:1 mixture of E and Z isomers respectively (336 mg, 76%) $^1$H-NMR (400 MHz, CDCl$_3$) 7.50-7.45 (2H, m, 2×ArH), 7.40-7.30 (3H, m, 3×ArH), 6.61 (0.7H, dt, J 15.7 and 7.1, vinylic H), 6.24 (0.3H, s, HC=CO), 6.16 (0.7H, s, HC=CO), 6.07-5.99 (0.3H, m, vinylic H), 6.00 (0.7H, dt, J 16.1 and 1.5, vinylic H), 5.92 (0.3H, dt, J 11.6 and 1.5, vinylic H), 5.28 (0.6H, s, OCH2Ar), 5.25 (1.4H, s, OCH2Ar), 2.46 (0.5H, ddd, J 15.2, 7.6 and 1.5, allylic H), 2.24 (1.5H, ddd, J 15.2, 7.6 and 1.5, allylic H), 1.52-1.42 (2H, m, CH2), 1.40-1.22 (14H, m, 7×CH2), 0.90 (3H, t, J 7.1, CH3).

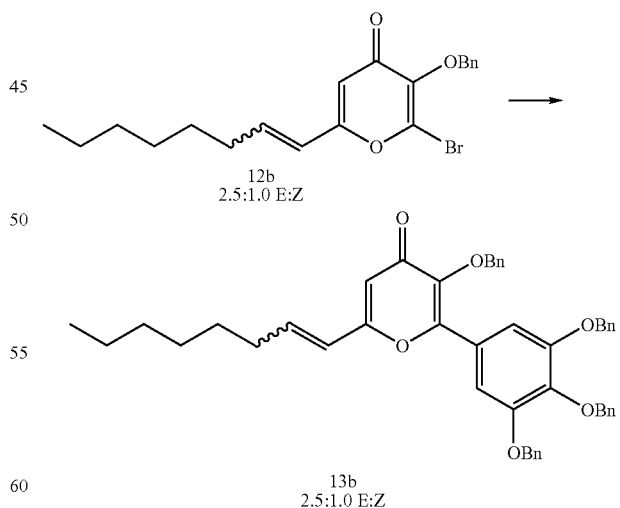

A suspension of 12b (251 mg, 0.64 mmol, 1.00 eq.), Pd(PPh3)4 (69 mg, 0.06 mmol, 10 mol %) and K2CO3 (283 mg, 2.05 mmol, 3.20 eq.) in DMF/H2O (2:1, 5.1 mL) was degassed for 5 mins, then a degassed solution of boronic acid (310 mg, 0.71 mmol, 1.10 eq.) in DMF (1.8 mL) and the reaction was heated to 60° C. and stirred for 4 hours. The reaction was cooled to room temperature, diluted with water (20 mL) and extracted with EtOAc (2×20 mL). The combined organic extracts were dried (MgSO4) and concentrated in vacuo. Purification by flash chromatography (10% EtOAc: 90% petrol→20% EtOAc:80% petrol→30% EtOAc:70% petrol→40% EtOAc:60% petrol) gave the title compound as a yellow oil (332 mg, 74%) $^1$H-NMR (400 MHz, CDCl$_3$) 7.48-7.20 (22H, m, 22×ArH), 6.52-5.90 (3H, m, vinylic H and pyranone H), 5.32-4.92 (8H, m, 4×OCH2Ar), 2.60-2.20 (2H, m, CH2), 1.58-1.40 (2H, m, CH2), 1.40-1.20 (6H, m, 3×CH2), 1.00-0.80 (3H, m, CH3).

petrol→40% EtOAc:60% petrol) gave the title compound as a yellow oil (260 mg, 74%) $^1$H-NMR (400 MHz, CDCl$_3$) 7.50-7.20 (22H, m, 22×ArH), 6.50-6.00 (3H, m, 3×vinylic H), 5.30-4.90 (6H, m, OCH2Ar), 2.56-2.48 (0.4H, m, CH2), 2.28-2.20 (1.4H, m, CH2), 1.57-1.40 (2H, m, CH2), 1.40-1.20 (14H, m, 7×CH2), 0.92-0.84 (3H, m, CH3).

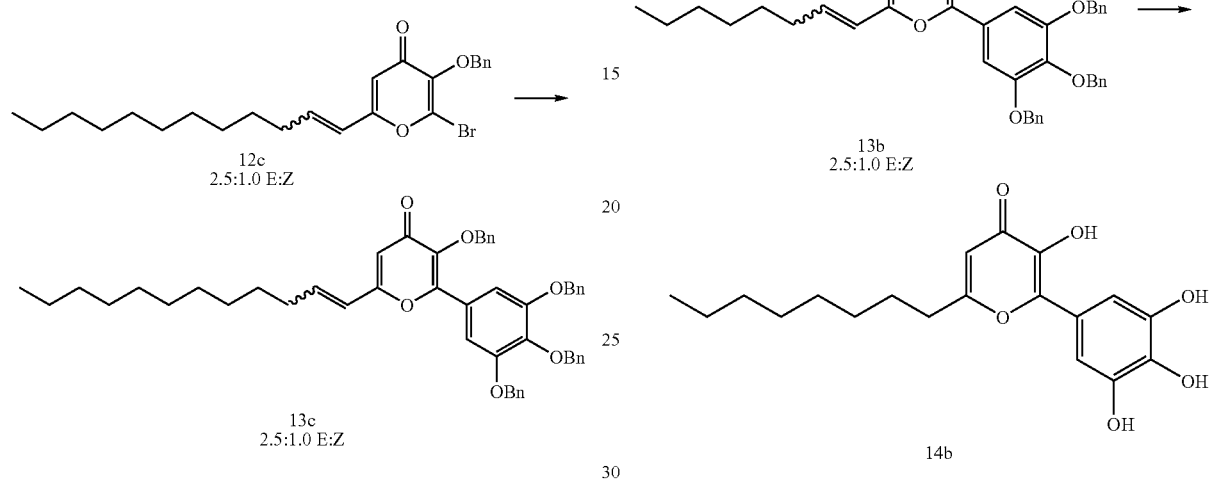

A suspension of 12c (204 mg, 0.46 mmol, 1.00 eq.), Pd(PPh3)4 (53 mg, 0.05 mmol, 10 mol %) and K2CO3 (203 mg, 1.47 mmol, 3.20 eq.) in DMF/H2O (2:1, 5.1 mL) was degassed for 5 mins, then a degassed solution of boronic acid 221 mg, 0.50 mmol, 1.10 eq.) in DMF (1.8 mL) and the reaction was heated to 60° C. and stirred for 4 hours. The reaction was cooled to room temperature, diluted with water (20 mL) and extracted with EtOAc (2×20 mL). The combined organic extracts were dried (MgSO4) and concentrated in vacuo. Purification by flash chromatography (10% EtOAc: 90% petrol→20% EtOAc:80% petrol→>30% EtOAc:70%

13b (320 mg, 0.45 mmol, 1.00 eq.) was dissolved in the minimal amount of ethyl acetate and taken into MeOH (10 mL). 10% Pd/C (180 mg) was slurried with MeOH (1 mL) and added to the solution. The solution was evacuated and backfilled with H2 3 times and stirred for 1 hour. The suspension was filtered through Celite® and concentrated in vacuo to yield 14b as a tan solid (105 mg, 67%) $^1$H-NMR (400 MHz, d$^6$-DMSO/D2O shake) 7.06 (2H, s, 2×ArH), 6.24 (1H, s, vinylic H), 2.59 (2H, t, J 7.1, CH2), 1.64 (2H, quintet, J 7.1, CH2), 1.30-1.10 (10H, m, 5×CH2), 0.81 (3H, t, J 7.1, CH3).

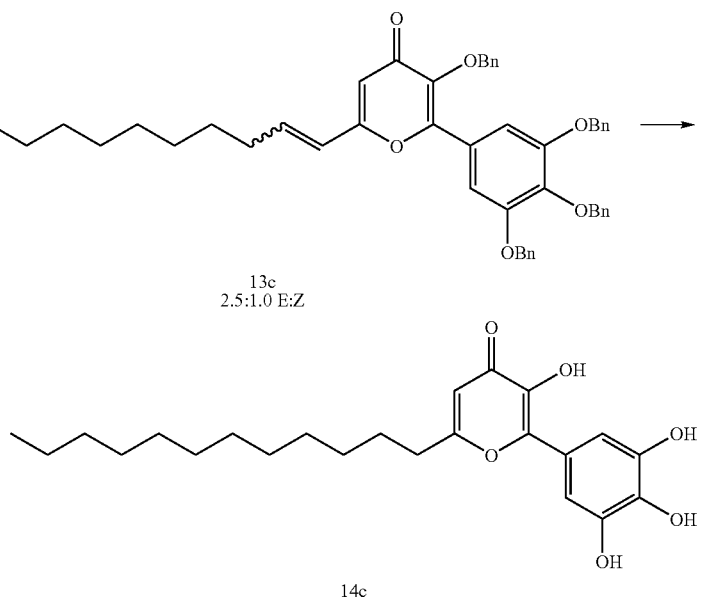

13c (250 mg, 0.33 mmol, 1.00 eq.) was dissolved in the minimal amount of ethyl acetate and taken into MeOH (10 mL). 10% Pd/C (150 mg) was slurried with MeOH (1 mL) and added to the solution. The solution was evacuated and backfilled with H2 3 times and stirred for 1 hour. The suspension was filtered through Celite® and concentrated in vacuo to yield 14c as a tan solid (84 mg, 63%) $^1$H-NMR (400 MHz, d$^6$-DMSO/D2O shake) 7.08 (2H, s, 2×ArH), 6.24 (1H, s, vinylic H), 2.59 (2H, t, J 7.1, CH2), 1.64 (2H, quintet, J 7.1, CH2), 1.37-1.00 (18H, m, 9×CH2), 0.81 (3H, t, J 7.1, CH3).

EXPERIMENTAL

The following experiments were conducted to demonstrate the protective effective of certain antioxidant compounds in relation to oxidative stress-induced cytotoxicity in mouse embryonic stem cells:

Oxidative stress and related free radical damage can be induced in cells, including stem cells, by exposing the cells to tert-butyl hydroperoxide in the incubation medium. Decomposition of the peroxide over a period of time leads to a steady generation of reactive oxygen species. This in turn triggers a cascade of free radical-mediated events that eventually leads to irreversible damage and ultimately cell death as the natural antioxidant defences are overwhelmed.

The extent of cytotoxicity induced by peroxide exposure can be quantified using a number of well-documented assays, including the MTT protocol. This is a colorometric assay that measures the reduction of MTT to formazan, a process that can only occur when cells are viable. Thus, by comparing the amount of formazan produced in control cells, against cells treated with a cytotoxic agent, such as tert-butyl hydroperoxide, the reduction in cell viability induced by the agent can be measured.

The assay can be further extended to determine the effectiveness of compounds to provide protection against cytotoxic agents. In the case of the novel antioxidants, the subject of this patent, this can be achieved by pre-incubation of the cells with the antioxidant agent prior to induction of oxidative stress by tert-butyl hydroperoxide. Thus a comparison of the amount of formazan produced by control cells against cells with the cytotoxic peroxide present, plus or minus pre-incubation with the novel antioxidant, can determine the extent by which the compound can retain cell viability.

Mechanism of MTT assay

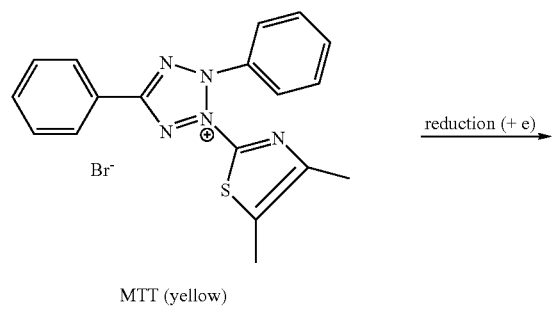

MTT (yellow)

reduction (+ e) →

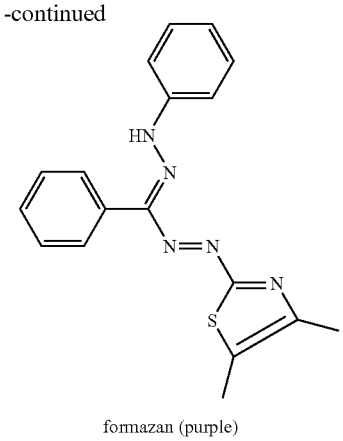

formazan (purple)

(3-(4,5-Dimethylthiazol-2-yl)-2,5-diphenyltetrazolium bromide)

A 96-well plate was seeded with approximately 20,000 mouse embryonic stem cells per well and left to grow at 37° C. (5% $CO_2$) overnight. Antioxidants, denoted as Exp.1, Exp.2 and Exp.3, were dissolved in DMSO and added to the wells in triplicate 30 min before induction of oxidative stress with tert-butyl hydroperoxide. The resultant concentrations of the tested antioxidants in the wells were 0.1, 0.5 and 1 µM. Controls were also initiated using cell medium (DMEM$^+$)/DMSO. After the 30 min pre-incubation period, tert-butyl peroxide was added to the wells to provide a final concentration of 400 µM. The plated cells were returned to the incubator (37° C.) for 90 min. After this period, 20 µL of the MTT reagent solution was added to all of the wells. The plate was then further incubated for a further 3 hours. The supernatant was removed from the wells and 200 µl DMSO added to all wells to solubilise reduced MTT (formazan). The plate was protected from light and shaken for 10 min. The supernatant was removed from the wells and aliquoted into a new 96-well plate for the colorometric measurements. Absorbance was determined at 540 nm.

RESULTS AND DISCUSSION

The average corrected absorbance. (0.737) for the DMEM$^+$ control (which contained no antioxidant compounds or tert-butyl hydroperoxide) represented the 100% viability benchmark. Comparison of the corrected absorbances in the various well treatment regimes relative to that of the DMEM$^+$ control enabled the resultant effects on cell viability to be calculated. tBHP=tert-butyl hydroperoxide.
From Table 1, exposure to tert-butyl hydroperoxide reduces cell viability to 37% of the control. At a concentration of 1 µM in the incubation medium without the peroxide present, neither Exp.1 nor Exp.2 had a negative impact on viability indicating that neither compound induced cytotoxicity at that level of exposure.

Exp.1, Exp.2 and Exp.3 all exhibited a strong protective effect from the oxidative stress-induced cytotoxicity of tert-butyl hydroperoxide. Exp.2 was of particular note in this respect and was able to almost fully reverse the loss of cell viability induced by tert-butyl hydroperoxide (96.9%+/−3.9 sd). A concentration dependence effect was observed.

In respect of structure activity relationships, it is evident that the dodecyl chain of Exp.2 imparts greater efficacy than the octyl chain of Exp.3. A key finding of these results is in relation to the literature on natural flavonoids in which a number of authors have alluded to the importance of the A-ring of the flavonoid as being an integral component of the antioxidant activity of the molecule (as exemplified in "Structure-Antioxidant Activity Relationships Of Flavonoids And Phenolic Acids; Rice-Evans et al.; Free Radical Biology & Medicine, Vol. 20, No. 7, pp 933-956, 1996")

The data presented here unequivocally demonstrates that the A-ring constituent is not pre-requisite and can be completely removed from the molecule with retention of potent antioxidant bio-activity. Comparison of Exp.1 relative to Exp.2 in this cell viability oxidative stress assay indicates that the activity may not just be preserved by removal of the A-ring, but enhanced.

TABLE 1

| Treatments | Ave. Absorbance | Ave. Corrected Absorbance | Std Dev. (±) | Ave. Cell Viability (%) | Std Dev. (±) |
|---|---|---|---|---|---|
| Controls | | | | | |
| DMEM+ | 0.811 | 0.737 | 0.027 | 100.0 | 3.6 |
| 400 µM tBHP | 0.347 | 0.273 | 0.010 | 37.0 | 1.3 |
| 1 µM Exp.1 (No tBHP) | 0.866 | 0.791 | 0.015 | 107.4 | 2.0 |
| 1 µM Exp.2 (No tBHP) | 0.841 | 0.767 | 0.044 | 104.1 | 5.9 |
| Exp. 1 (µM) 400 µM tBHP | | | | | |
| 0.1 | 0.494 | 0.420 | 0.042 | 56.9 | 5.7 |
| 0.5 | 0.712 | 0.638 | 0.041 | 86.5 | 5.5 |
| 1 | 0.700 | 0.625 | 0.026 | 84.8 | 3.5 |
| Exp. 2 (µM) 400 µM tBHP | | | | | |
| 0.1 | 0.520 | 0.446 | 0.013 | 60.5 | 1.7 |
| 0.5 | 0.773 | 0.699 | 0.047 | 94.8 | 6.4 |
| 1 | 0.788 | 0.714 | 0.029 | 96.9 | 3.9 |
| Exp. 3 (µM) 400 µM tBHP | | | | | |
| 0.1 | 0.328 | 0.254 | 0.020 | 34.4 | 2.7 |
| 0.5 | 0.483 | 0.409 | 0.031 | 55.5 | 4.2 |
| 1 | 0.593 | 0.519 | 0.026 | 70.4 | 3.5 |

Compounds Tested
Exp.1:

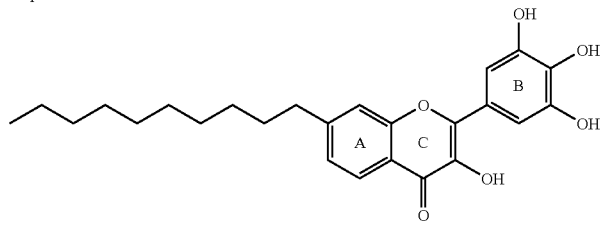

Exp.2:

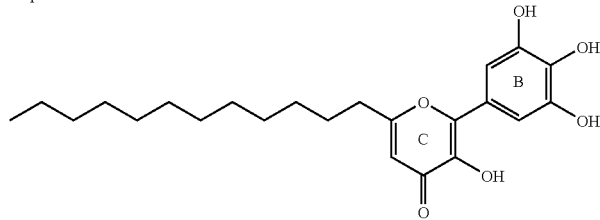

Exp.3:

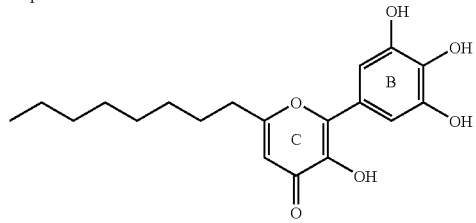

What is claimed:

1. A method of in vitro preservation of living animal cells in a viable non-terminally differentiated state, said method comprising contacting living non-terminally differentiated animal cells with a compound of Formula I or a salt thereof:

Formula I wherein:
A) $R_{12}$ and $R_{26}$ each independently represent —OH or a glycosidic functional group;
$R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$alkoxy-, hydroxy-$C_{1-6}$ alkyl-, $C_{1-6}$alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;

B) either a):
$R_{20}$ represents H or a $C_{2-30}$ saturated or unsaturated hydrocarbon chain;
$R_{21}$:
i) represents H;
ii) together with $R_{22}$ provides a second bond between $C^1$ and $C^2$; or
iii) when X is —$NR_1$— and $R_1$ is not H or $C_{1-6}$alkyl, together with $R_1$ provides a second bond between $C^1$ and N;
$R_{22}$:
i) represents H;
ii) together with $R_{23}$ forms =O; or
iii) together with $R_{21}$ provides a second bond between $C^1$ and $C^2$;
$R_{23}$:
i) represents H or a $C_{2-30}$ saturated or unsaturated hydrocarbon chain;
ii) together with $R_{22}$ forms =O;
wherein at least one of $R_{20}$ and $R_{23}$ is a $C_{2-30}$ saturated or unsaturated hydrocarbon chain;
or b):
$R_{20}$, $R_{21}$, $R_{22}$, and $R_{23}$, together with $C^1$ and $C^2$, form a 5, 6 or 7 membered unsaturated-ring, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, hydroxyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;

C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;

D) X is —O—, —S— or —$NR_1$—, wherein $R_1$ i) represents H or $C_{1-6}$alkyl, or ii) together with $R_{21}$ provides a second bond between $C^1$ and N;

wherein said $C_{2-30}$ saturated or unsaturated hydrocarbon chain of $R_{20}$, $R_{23}$ and the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —$CO_2H$, —$CO_2C_{1-6}$alkyl, —$S(O)_2C_{1-6}$alkyl, —$S(O)_2$phenyl, —$SC_{1-6}$alkyl, —$NO_2$, —OH, —CF3, —$N(R_2)(R_3)$, —$NHC(O)NHC_{1-6}$alkyl, —$C(O)N(R_2)(R_3)$, imine and substituted or unsubstituted triphenylphosphonium; and wherein one or more available —$CH_2$-groups present in the $C_{2-30}$ hydrocarbon chain of $R_{20}$, $R_{23}$ and the 5, 6 or 7 membered unsaturated ring is optionally and independently replaced by —O—, —C(O)—, —$S(O)_p$—, or —$N(R_2)$— provided always that no two such replacements in the resulting chain are consecutive; wherein $R_2$ and $R_3$ each independently represent H or $C_{1-6}$alkyl, and wherein p is 0 to 2; and wherein the total number of =O on ring C is no greater than 1.

2. The method of claim 1, wherein X represents —O—.

3. The method of claim 1, wherein $R_{12}$ and $R_{26}$ both represent —OH.

4. The method of claim 1, wherein one of $R_{12}$ and $R_{26}$ represents —OH and the other of $R_{12}$ and $R_{26}$ represents a glycosidic functional group.

5. The method of claim 1, wherein n=1.

6. The method of claim 1, wherein n=0.

7. The method of claim 1, wherein:
$R_{20}$ represents H or a $C_{2-30}$ saturated or unsaturated hydrocarbon chain;
$R_{21}$:
i) represents H; or
ii) together with $R_{22}$ provides a second bond between $C^1$ and $C^2$;
$R_{22}$:
i) represents H;
ii) together with $R_{23}$ forms =O; or
iii) together with $R_2$ provides a second bond between $C^1$ and $C^2$; and
$R_{23}$:
i) represents H or a $C_{2-30}$ saturated or unsaturated hydrocarbon chain; or
ii) together with $R_{22}$ forms =O.

8. The method of claim 1, wherein $R_{20}$, $R_{21}$, $R_{22}$ and $R_{23}$, together with $C^1$ and $C^2$, form a 5, 6 or 7 membered unsaturated-ring.

9. The method of claim 8, wherein said unsaturated-ring is substituted with a $C_{2-30}$ saturated or unsaturated hydrocarbon chain at the meta or para position relative to $C^1$ or wherein said unsaturated ring is substituted with $C_{2-15}$ saturated or unsaturated hydrocarbon chains at two of the ortho, meta and para positions relative to $C^1$.

10. The method of claim 1, wherein said $C_{2-30}$ saturated or unsaturated hydrocarbon chain of $R_{20}$, $R_{23}$ and the 5, 6 or 7 membered unsaturated ring comprises a —$CH_2$-group connecting to $C^1$, $C^2$ or the 5, 6 or 7 membered ring.

11. The method of claim 10, wherein said $C_{2-30}$ saturated or unsaturated hydrocarbon chain of $R_{20}$, $R_{23}$ and the 5, 6 or 7 membered unsaturated ring is unsubstituted.

12. The method of claim 11, wherein said $C_{2-30}$ saturated or unsaturated hydrocarbon chain of $R_{20}$, $R_{23}$ and the 5, 6 or 7 membered unsaturated ring is saturated.

13. The method of claim 10, wherein said $C_{2-30}$ saturated or unsaturated hydrocarbon chain of $R_{20}$, $R_{23}$ and the 5, 6 or 7 membered unsaturated ring is a straight hydrocarbon chain comprising 6 to 15 carbon atoms.

14. The method of claim 1, wherein the living animal cells are stem cells.

15. The method of claim 14, wherein the stem cells are selected from the group consisting of embryonic stem cells (ESCs), adult stem cells and induced pluripotent stem (iPS) cells.

16. The method of claim 15, wherein the embryonic stem cells are human embryonic stem cells or mouse embryonic stem cells.

17. The method of claim 15, wherein the stem cells are induced pluripotent stem (iPS) cells.

18. The method of claim 1, wherein the living animal cells are de-differentiated cells.

19. A compound of Formula Ia or a salt thereof:

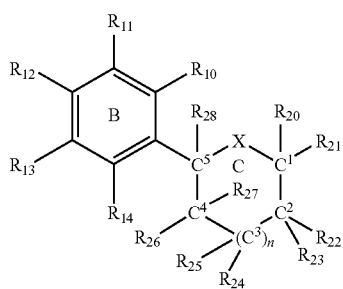

Formula Ia wherein:
i. $R_{12}$ and $R_{26}$ each independently represent —OH or a glycosidic functional group;
$R_{10}$, $R_{11}$, $R_{13}$, and $R_{14}$ each independently represent H, —OH, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde groups; and wherein ring B comprises no more than one glycosidic functional group;
ii. either a):
$R_{20}$ represents H or a $C_{2-30}$ saturated or unsaturated hydrocarbon chain;
$R_{21}$:
i) represents H;
ii) together with $R_{22}$ provides a second bond between $C^1$ and $C^2$; or
iii) when X is —$NR_1$— and $R_1$ is not H or $C_{1-6}$alkyl, together with $R_1$ provides a second bond between $C^1$ and N;
$R_{22}$:
i) represents H;
ii) together with $R_{23}$ forms =O; or
iii) together with $R_2$, provides a second bond between $C^1$ and $C^2$;

$R_{23}$:
i) represents H or a $C_{2-30}$ saturated or unsaturated hydrocarbon chain;
ii) together with $R_{22}$ forms =O;
wherein at least one of $R_{20}$ and $R_{23}$ is a $C_{2-30}$ saturated or unsaturated hydrocarbon chain;
or b):
$R_{20}$, $R_{21}$, $R_{22}$, and $R_{23}$, together with $C^1$ and $C^2$, form a 5, 6 or 7 membered unsaturated-ring, which ring is substituted with a group which is a $C_{2-30}$ saturated or unsaturated hydrocarbon chain, which ring is optionally and independently further substituted with one or more groups selected from nitro, halogen, amino, amido, cyano, carboxyl, sulphonyl, ketone, aldehyde and saturated or unsaturated $C_{2-15}$ hydrocarbon chain, which $C_{2-15}$ hydrocarbon chain may be substituted with one or more of nitro, halogen, amino, amido, cyano, carboxyl, sulphonyl, hydroxyl, ketone, aldehyde or nitrone groups;
C) n is 0 or 1, wherein when n is 0, either i) $R_{27}$ and $R_{28}$ represent H or ii) $R_{27}$ together with $R_{28}$ provide a second bond between $C^4$ and $C^5$; or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{28}$ represents —OH and X is —O—;
D) X is —O—, —S— or —$NR_1$—, wherein $R_1$ i) represents H or $C_{1-6}$alkyl, or ii) together with $R_2$, provides a second bond between $C^1$ and N;
wherein said $C_{2-30}$ saturated or unsaturated hydrocarbon chain of $R_{20}$, $R_{23}$ and the 5, 6 or 7 membered unsaturated ring is optionally and independently substituted with one or more groups selected from $C_{1-6}$ alkyl, $C_{1-6}$alkoxy, hydroxy-$C_{1-6}$ alkyl, Cl, F, Br, I, —CN, —$CO_2H$, —$CO_2C_{1-6}$alkyl, —$S(O)_2C_{1-6}$alkyl, —$S(O)_2$-phenyl, —$SC_{1-6}$alkyl, —$NO_2$, —OH, —$CF_3$, —$N(R_2)(R_3)$, —$NHC(O)NHC_{1-6}$alkyl, —$C(O)N(R_2)(R_3)$, imine and substituted or unsubstituted triphenylphosphonium; and wherein one or more available —$CH_2$— groups present in the $C_{2-30}$ hydrocarbon chain of $R_{20}$, $R_{23}$ and the 5, 6 or 7 membered unsaturated ring is optionally and independently replaced by —O—, —$C(O)$—, —$S(O)_p$—, or —$N(R_2)$— provided always that the resulting chain includes a —$CH_2$— group connecting to $C^1$, $C^2$ or the 5, 6 or 7 membered ring and no two such replacements are consecutive; wherein $R_2$ and $R_3$ each independently represent H or $C_{1-6}$alkyl, and wherein p is 0 to 2;
and wherein the total number of =O on ring C is no greater than 1;
provided that when i) n=1, ii) X represents —O—, iii) $R_{12}$ represents —OH, iv) $R_{24}$ together with $R_{25}$ represent =O, v) $R_{20}$, $R_{21}$, $R_{22}$ and $R_{23}$ form a benzene ring including $C^1$ and $C^2$, and vi) said benzene ring is substituted with at least one group which is a $C_{2-30}$ saturated or unsaturated hydrocarbon chain, then:
said $C_{2-30}$ saturated or unsaturated hydrocarbon chain is substituted with one or more groups selected from $C_{1-6}$alkoxy, hydroxy-$C_{1-6}$ alkyl, Cl, F, Br, I, —CN, —$CO_2H$, sulphonyl, —$CO_2C_{1-6}$alkyl, —$S(O)_2C_{1-6}$alkyl, —$S(O)_2$phenyl, —$SC_{1-6}$alkyl, —$NO_2$, —OH, —$CF_3$, —$N(R_2)(R_3)$, —$NHC(O)NHC_{1-6}$alkyl, —$C(O)N(R_2)(R_3)$, imine and substituted or unsubstituted triphenylphosphonium; and/or wherein one or more available —$CH_2$— groups present in said $C_{2-30}$ hydrocarbon chain is replaced by —O—, —$C(O)$—, —$S(O)_p$—, or —$N(R_2)$—; wherein $R_2$ and $R_3$ each independently represent H or $C_{1-6}$alkyl, and wherein p is 0 to 2; and/or said benzene ring is substituted with one or more groups selected from nitro, halogen, amino, amido, cyano, carboxyl, sulphonyl, ketone, aldehyde and saturated or unsaturated $C_{1-6}$ hydrocarbon chain, which $C_{1-6}$ hydrocarbon chain is substituted with one or more of nitro, halogen, amino, amido, cyano, carboxyl, sulphonyl, hydroxyl, ketone, aldehyde or nitrone groups.

20. The compound of claim 19, wherein X represents —O—.

21. The compound of claim 19, wherein $R_{12}$ and $R_{26}$ both represent —OH.

22. The compound of claim 19, wherein one of $R_{12}$ and $R_{26}$ represents —OH and the other of $R_{12}$ and $R_{26}$ represents a glycosidic functional group.

23. The compound of claim 19, wherein n=1.

24. The compound of claim 19, wherein n=0.

25. The compound of claim 19, wherein:
$R_{20}$ represents H or a $C_{2-30}$ saturated or unsaturated hydrocarbon chain;
$R_{21}$:
  i) represents H; or
  ii) together with $R_{22}$ provides a second bond between $C^1$ and $C^2$;
$R_{22}$:
  i) represents H;
  ii) together with $R_{23}$ forms =O; or
  iii) together with $R_{21}$ provides a second bond between $C^1$ and $C^2$; and
$R_{23}$:
  i) represents H or a $C_{2-30}$ saturated or unsaturated hydrocarbon chain; or
  ii) together with $R_{22}$ forms =O.

26. The compound of claim 19, wherein $R_{20}$, $R_{21}$, $R_{22}$ and $R_{23}$, together with $C^1$ and $C^2$, form a 5, 6 or 7 membered unsaturated-ring.

27. The compound of claim 26, wherein said unsaturated-ring is substituted with a $C_{2-30}$ saturated or unsaturated hydrocarbon chain at the meta or para position relative to $C^1$ or wherein said unsaturated ring is substituted with $C_{2-15}$ saturated or unsaturated hydrocarbon chains at two of the ortho, meta and para positions relative to $C^1$.

28. The compound of claim 19, wherein said $C_{2-30}$ saturated or unsaturated hydrocarbon chain of $R_{20}$, $R_{23}$ and the 5, 6 or 7 membered unsaturated ring comprises a —CH$_2$— group connecting to $C^1$, $C^2$ or the 5, 6 or 7 membered ring.

29. The compound of claim 28, wherein said $C_{2-30}$ saturated or unsaturated hydrocarbon chain of $R_{20}$, $R_{23}$ and the 5, 6 or 7 membered unsaturated ring is unsubstituted.

30. The compound of claim 29, wherein said $C_{2-30}$ saturated or unsaturated hydrocarbon chain of $R_{20}$, $R_{23}$ and the 5, 6 or 7 membered unsaturated ring is saturated.

31. The compound of claim 29, wherein said $C_{2-30}$ saturated or unsaturated hydrocarbon chain of $R_{20}$, $R_{23}$ and the 5, 6 or 7 membered unsaturated ring is a straight hydrocarbon chain comprising 6 to 15 carbon atoms.

\* \* \* \* \*